United States Patent
Karrer et al.

(10) Patent No.: US 6,306,798 B1
(45) Date of Patent: Oct. 23, 2001

(54) COMPOUNDS FOR CONTROLLING INSECTS AND REPRESENTATIVES OF THE ORDER ACARINA

(75) Inventors: Friedrich Karrer, Zofingen; Roger Graham Hall, Pfeffingen, both of (SE)

(73) Assignee: Syngenta Crop Protection, Inc., Greensboro ( * ) Notice: Subject to any disclaimer, the term of this patent is extended or adjusted under 35 U.S.C. 154(b) by 0 days.

(21) Appl. No.: 09/230,311

(22) PCT Filed: Jul. 15, 1997

(86) PCT No.: PCT/EP97/03772

§ 371 Date: Jan. 21, 1999

§ 102(e) Date: Jan. 21, 1999

(87) PCT Pub. No.: WO98/03475

PCT Pub. Date: Jan. 29, 1998

(30) Foreign Application Priority Data

Jul. 24, 1996 (SE) .................................................. 1853/96
Mar. 13, 1997 (SE) .................................................. 607/97

(51) Int. Cl.$^7$ .......................... A01N 33/26; C07C 255/66
(52) U.S. Cl. .............................................. 504/312; 558/391
(58) Field of Search ............................. 558/391; 504/312

(56) References Cited

U.S. PATENT DOCUMENTS

| | | |
|---|---|---|
| 3,870,505 | 3/1975 | Kaugars . |
| 4,264,326 | 4/1981 | Rau . |
| 4,290,770 | 9/1981 | Rau . |
| 4,309,181 | 1/1982 | Rau . |
| 5,340,837 | 8/1994 | Hall et al. . |

FOREIGN PATENT DOCUMENTS

| | | |
|---|---|---|
| 2831067 | 2/1979 | (DE) . |
| 3001265 | 7/1980 | (DE) . |
| 3001266 | 7/1980 | (DE) . |
| 581725 | 2/1994 | (EP) . |
| 604798 | 7/1994 | (EP) . |
| 709372 | 5/1996 | (EP) . |
| 2471400 | 6/1981 | (FR) . |

OTHER PUBLICATIONS

J. Med. Chem., vol. 24, No. 5, D. L. Rector, May 1981, pp. 532–538.
C.R.A. Sciences, C, vol. 277, No. 8, Aug. 27, 1973, pp. 319–322.
J. Agr. Food Chem., vol. 21, No. 4, 1973, pp. 647–650.
Tetrahedron, vol. 52, No. 2, 1996, pp. 661–668.
Derwent Abstract 81–57340D/198132 (of FR2471400, 1981.
Chemical Abstract 79:137067 (of C.R.A. Sciences, C, vol. 277, No. 8, Aug. 27, 1973, pp. 319–322).
Jadhav et al., CA 125:114101, Feb./.Mar. 1996.*
Nishiwaki et al., CA 123:313900, 1995.*
Stejskalova et al., CA 117:131119, 1992.*
Grajcar et al., CA 100:211619, 1984.*
Dubenko et al., CA 96:99275, 1982.*
Shawali et al., CA 94:208778, 1981.*
Remnikov et al., CA 94:188797, 1981.*
Barbey et al., CA 94:64840, 1981.*
Barbey et al., CA 91:192464, 1979.*
Bhaskare et al., CA 83:125617, 1975.*
Bhaskare et al., CA 83:107665, 1975.*
Bhaskare et al., CA 83:107663, 1975.*
Beu et al., CA 83:8650, 1975.*
Barbey et al., CA 81:98559, 1974.*
Bazavova et al., CA 80:120455, 1974.*
Beu et al., CA 79:31068, 1973.*
Ried et al., CA 72:12287, 1970.*

* cited by examiner

Primary Examiner—Laura L. Stockton
(74) Attorney, Agent, or Firm—William A. Teoli, Jr.

(57) ABSTRACT

A composition, which comprises at least one compound of the formula

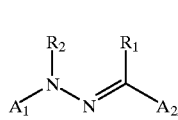

(I)

in which $A_1$, $A_2$, $R_1$ and $R_2$ are as defined in claim 1, or, if appropriate, an E/Z isomer, an E/Z isomer mixture and/or a tautomer thereof, in each case in free form or in agrochemically utilizable salt form, as active ingredient and at least one auxiliary, can used for pest control.

4 Claims, No Drawings

COMPOUNDS FOR CONTROLLING INSECTS AND REPRESENTATIVES OF THE ORDER ACARINA

This application is a 371 of PCT/EP97/03772 filed Jul. 15, 1997.

The invention relates to a pesticidal composition which comprises at least one compound of the formula

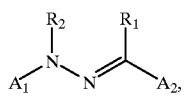

(I)

in which

- $A_1$ and $A_2$ are independent of one another and are in each case a mono- or bicyclic aryl or hetaryl radical, each hetaryl radical independently of the other having 1 up to and including 4 hetero atoms selected from the group consisting of N, O and S;
- $A_1$ is substituted with a substituent $(R_{3a})_{n1}$ and $A_2$ with a substituent $(R_{3b})_{n2}$;
- $R_1$ is —CN, halo-$C_1$–$C_6$alkyl or —C(=S)—N($R_5$)$_2$ (in which the two $R_5$ are independent of one another);
- $R_2$ is hydrogen, —OH, $C_1$–$C_6$alkyl, $C_1$–$C_6$alkoxy, $C_3$–$C_6$cycloalkyl, $C_3$–$C_6$alkenyl, $C_3$–$C_6$alkynyl, halo-$C_1$–$C_6$alkyl, halo-$C_3$–$C_6$alkenyl, halo-$C_3$–$C_6$alkynyl, benzyl or benzoyl, in which the benzyl or benzoyl radical is unsubstituted or mono- to trisubstituted in the aromatic ring by substituents which are independent of one another and selected from the group consisting of halogen, —CN, NO$_2$, $C_1$–$C_6$alkyl, $C_1$–$C_6$alkoxy, halo-$C_1$–$C_6$alkyl and halo-$C_1$–$C_6$alkoxy; $C_1$–$C_6$alkoxy-$C_1$–$C_6$alkyl, cyano-$C_1$–$C_6$alkyl, —C(=X)—$R_7$, —OC(=O)—$R_7$, —C(=O)—C(=O)—$R_7$, —S(=O)$_p$N($R_6$)$_2$ (in which the two $R_6$ are independent of one another); cyano, —C$_1$–C$_6$alkyl-N($R_{10}$)—C(=O)—$R_8$, —C$_1$–C$_6$alkyl-S—C(=S)—$R_8$, —C$_1$–C$_6$alkyl-S(=O)$_p$—$R_9$, —S(=O)$_p$—$R_9$, or —CH$_2$—N($R_{10}$)—SO$_2$—$R_9$;
- $R_{3a}$ and $R_{3b}$ are independently of each other halogen, $C_1$–$C_6$alkyl, $C_2$–$C_4$alkenyl, $C_2$–$C_4$alkynyl, halo-$C_1$–$C_6$alkyl, halo-$C_2$–$C_4$alkenyl, halo-$C_2$–$C_4$alkynyl, $C_1$–$C_6$alkoxy, halo-$C_1$–$C_6$alkoxy, $C_2$–$C_6$alkenyloxy, $C_2$–$C_6$alkynyloxy, halo-$C_2$–$C_6$alkenyloxy, halo-$C_2$–$C_6$alkynyloxy, —OH, —SF$_5$, —CHO, —C(=O)—$C_1$–$C_6$alkyl, —C(=O)-halo-$C_1$–$C_6$alkyl, —C(=O)—OC$_1$–$C_6$alkyl, —C(=O)—O-halo-$C_1$–$C_6$alkyl, —O—C(=O)N($R_6$)$_2$ (in which the two $R_6$ are independent of one another), —CN, —NO$_2$, —S(=O)$_2$N($R_6$)$_2$ (in which the two $R_6$ are independent of one another), —S(=O)$_p$—$C_1$–$C_6$alkyl, —S(=O)$_p$-halo-$C_1$–$C_6$alkyl, —O—S(=O)$_p$—$C_1$–$C_6$alkyl, —O—S(=O)$_p$-halo-$C_1$–$C_6$alkyl, phenyl, benzyl, phenoxy or benzyloxy, each of the phenyl, benzyl, phenoxy or benzyloxy radicals being unsubstituted or mono- to penta-substituted in the aromatic ring by substituents which are independent of one another and selected from the group consisting of halogen, cyano, NO$_2$, $C_1$–$C_6$alkyl, halo-$C_1$–$C_6$alkyl, $C_1$–$C_6$alkoxy and halo-$C_1$–$C_6$alkoxy;
- $n_1$ and $n_2$ are 0 or, depending on the substitution options on the ring systems $A_1$ and $A_2$ in question, independently of each other 1, 2, 3, 4 or 5;
- X is O or S;
- p is 0, 1 or 2;
- $R_5$ radicals independently of one another are H or $C_1$–$C_8$alkyl;
- $R_6$ radicals independently of one another are H, $C_1$–$C_8$alkyl, $C_3$–$C_6$cycloalkyl, phenyl or benzyl, the phenyl or benzyl group in the aromatic ring being unsubstituted or mono- to trisubstituted by substituents which are independent of one another and selected from the group consisting of halogen, —CN, NO$_2$, $C_1$–$C_6$alkyl, $C_1$–$C_4$alkoxy, halo-$C_1$–$C_6$alkyl and halo-$C_1$–$C_6$alkoxy; or two alkyl radicals $R_6$ together with the nitrogen atom to which they are bonded form a five- to seven-membered ring in which a CH$_2$ group may be replaced by a hetero atom selected from the group consisting of O and S, or by NH, and where the five- to seven-membered ring is unsubstituted or mono- or di-substituted by $C_1$–$C_4$alkyl;
- $R_7$ is H, $C_1$–$C_8$alkyl, $C_2$–$C_8$alkenyl, halo-$C_1$–$C_8$alkyl, halo-$C_2$–$C_8$alkenyl, $C_1$–$C_8$alkoxy, halo-$C_1$–$C_8$alkoxy, $C_3$–$C_6$cycloalkyl, phenyl, benzyl, phenoxy, benzyloxy or —N($R_6$)$_2$ (in which the two $R_6$ are independent of one another);
- $R_8$ is $C_1$–$C_8$alkyl, $C_1$–$C_8$alkoxy, halo-$C_1$–$C_8$alkyl, halo-$C_1$–$C_8$alkoxy, $C_1$–$C_8$alkylthio, phenyl, benzyl or —N($R_6$)$_2$ (in which the two $R_6$ are independent of one another);
- $R_9$ is $C_1$–$C_6$alkyl, halo-$C_1$–$C_4$alkyl or aryl which is unsubstituted or mono- to trisubstituted by substituents which are independent of one another and selected from the group consisting of $C_1$–$C_6$alkyl, $C_2$–$C_4$alkenyl, $C_2$–$C_4$alkynyl, $C_1$–$C_4$alkoxy, halogen, cyano, halo-$C_1$–$C_4$alkyl, halo-$C_2$–$C_4$alkenyl, halo-$C_2$–$C_4$alkynyl, halo-$C_1$–$C_4$alkoxy and nitro; and
- $R_{10}$ is H, $C_1$–$C_6$alkyl, $C_3$–$C_6$cycloalkyl, phenyl or benzyl, the phenyl and benzyl radicals being unsubstituted or mono- to trisubstituted in the aromatic ring by substituents which are independent of one another and selected from the group consisting of $C_1$–$C_4$alkyl, $C_1$–$C_4$alkoxy, halogen, cyano, halo-$C_1$–$C_4$alkyl, halo-$C_1$–$C_4$alkoxy and nitro;

or, where appropriate, an E/Z isomer, E/Z isomer mixture and/or a tautomer thereof, in each case in free form or in agrochemically utilizable salt form, with the exception of 1-phenylhydrazono-2-nitroethylbenzene, as active ingredient and at least one auxiliary;

to compounds of the formula (Ia) defined below, E/Z isomers and/or tautomers thereof, in each case in free form or in salt form; to a process for the preparation and to the use of these compounds, E/Z isomers and tautomers; to a process for the preparation and to the use of these compositions; to intermediates, in free form or in salt form, for the preparation of these compounds, if appropriate to tautomers, in free form or in salt form, of these intermediates; and to a process for the preparation and to the use of these intermediates and tautomers thereof.

Certain phenylhydrazone derivatives are proposed in the literature as active ingredients in pesticides. However, the biological properties of these known compounds are not entirely satisfactory in the field of pest control, which is why there is a demand for providing further compounds which have pesticidal properties, in particular for controlling insects and representatives of the order Acarina, this object being achieved according to the invention by providing the present pesticides containing compounds of the formula (I).

Some compounds of the formula (I) contain asymmetric carbon atoms, which is why optically active forms of the compounds can occur. Owing to the presence of the C=N double bond, E- and Z-isomeric forms of the compounds may occur. Moreover, atropisomers of the compounds may occur. The formula (I) is intended to embrace all these isomeric forms which are possible and mixtures of these, for example racemates or E/Z isomer mixtures.

Unless otherwise defined, the general terms used hereinabove and hereinbelow have the meanings given in the following text.

Unless otherwise defined, carbon-containing groups and compounds contain in each case 1 up to and including 8, preferably 1 up to and including 6, in particular 1 up to and including 4, especially 1 or 2, carbon atoms.

Alkyl—as a group per se and as structural element of other groups and compounds, such as of haloalkyl, alkoxy or alkylthio—is, in each case with due consideration of the number of carbon atoms present in the relevant group or compound in every single case, either straight-chain, i.e. methyl, ethyl, propyl, butyl, pentyl or hexyl, or branched, e.g. isopropyl, isobutyl, sec-butyl, tert-butyl, isopentyl, neopentyl or isohexyl.

Alkenyl—as a group per se and as structural element of other groups and compounds, such as of alkenoxy, haloalkenyl or haloalkenoxy—is, in each case with due consideration of the number of carbon atoms present in the relevant group or compound in every single case, either straight-chain, e.g. vinyl, 1-methylvinyl, allyl, 1-butenyl or 2-hexenyl, or branched, e.g. isopropenyl.

Alkynyl—as a group per se and as structural element of other groups and compounds, such as haloalkynyl—is, in each case with due consideration of the number of carbon atoms present in the relevant group or compound in every single case, either straight-chain, e.g. propargyl, 2-butynyl or 5-hexynyl, or branched, e.g. 2-ethynylpropyl or 2-propargylisopropyl.

$C_3$–$C_6$-cycloalkyl is cyclopropyl, cyclobutyl, cyclopentyl or cyclohexyl.

Aryl is especially phenyl or naphthyl, in particular phenyl.

Monocyclic hetaryl has 1 up to and including 4 ring hetero atoms and is, for example, furyl, thienyl, pyridyl, imidazolyl, thiazolyl, oxazolyl, pyrimidyl, oxadiazolyl, thiadiazolyl, triazolyl or tetrazolyl.

Bicyclic hetaryl is to be understood as meaning a radical which contains 1 up to and including 4 hetero atoms either in only one ring—for example in quinolinyl, quinoxalinyl, indolinyl, benzothiophenyl or benzofuranyl—or in both rings—for example in pteridinyl or purinyl, the hetero atoms being independent of one another.

Halogen—as a group per se and as structural element of other groups and compounds, such as haloalkyl, haloalkenyl, haloalkynyl and haloalkoxy—is fluorine, chlorine, bromine or iodine, in particular fluorine, chlorine or bromine, especially fluorine or chlorine, very particularly chlorine.

Halogen-substituted carbon-containing groups and compounds, such as haloalkyl, haloalkenyl or haloalkynyl, can be partially halogenated or perhalogenated, it being possible for the halogen substituents to be identical or different in the case of polyhalogenation. Examples of haloalkyl—as a group per se and as structural element of other groups and compounds, such as haloalkenyl—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each of which is mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or an isomer thereof which is mono- to nonasubstituted by fluorine, chlorine and/or bromine, such as $CF(CF_3)CHFCF_3$ or $CH_2(CF_2)_2CF_3$. Haloalkenyl is, for example, $CH_2CH=CHCl$, $CH_2CH=CCl_2$, $CH_2CF=CF_2$ or $CH_2CH=CHCH_2Br$. Haloalkynyl is, for example, $CH_2C\equiv CF$, $CH_2C\equiv CCH_2Cl$ or $CF_2CF_2C\equiv CCH_2F$.

Those skilled in the art will be familiar with the fact that some compounds of the formula (I) can exist as tautomers, particularly when $R_2$ is H. The compounds of the formula (I) are therefore also to be understood as meaning, hereinabove and hereinbelow, the relevant tautomers, even when the latter are not mentioned specifically in each individual case.

Compounds of the formula (I) which have at least one basic centre can form, for example, acid addition salts. These acid addition salts are formed for example with strong inorganic acids, such as mineral acids, e.g. perchloric acid, sulfuric acid, nitric acid, nitrose acid, a phosphorus acid or a hydrohalic acid, with strong organic carboxylic acids, such as $C_1$–$C_4$alkanecarboxylic acids which are unsubstituted or substituted, for example by halogen, e.g. acetic acid, such as saturated or unsaturated dicarboxylic acids, e.g. oxalic, malonic, succinic, maleic, fumaric or phthalic acid, such as hydroxycarboxylic acids, e.g. ascorbic, lactic, malic, tartaric or citric acid, or such as benzoic acid, or with organic sulfonic acids, such as $C_1$–$C_4$alkanoic or arylsulfonic acids which are unsubstituted or substituted, for example by halogen, e.g. methane- or p-toluenesulfonic acid. Furthermore, compounds of the formula (I) which have at least one acidic group can form salts with bases. Suitable salts with bases are, for example, metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower-alkylamine, e.g. ethyl-, diethyl-, triethyl- or dimethylpropylamine, or with a mono-, di- or trihydroxy-lower-alkylamine, e.g. mono-, di- or triethanolamine. If appropriate, corresponding internal salts may furthermore be formed. Because of the close relation between the compounds of the formula (I) in free form and in the form of their salts, the free compounds of the formula (I) or salts thereof are to be understood as meaning, hereinabove and hereinbelow, in the spirit and for the purposes of the present invention, the corresponding salts or the free compounds of the formula (I), if so appropriate. The same applies to tautomers of compounds of the formula (I) and the salts of these tautomers. In general, the free form is preferred in each case.

Preferred within the scope of the invention are the following embodiments where—if necessary—$(R_3)_n$ in $A_1$ is designated $(R_{3a})_{n1}$ and $(R_3)_n$ in $A_2$ is designated $(R_{3b})_{n2}$, and where the proviso, that 1-phenylhydrazono-2-nitriloethylbenzene is excluded form the scope in each case applies:

(1) a pesticidal composition comprising at least one compound of the formula (I) in which $A_1$ and $A_2$ independently of one another are a substituent selected from the group consisting of

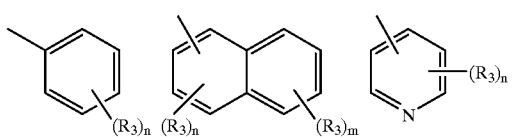

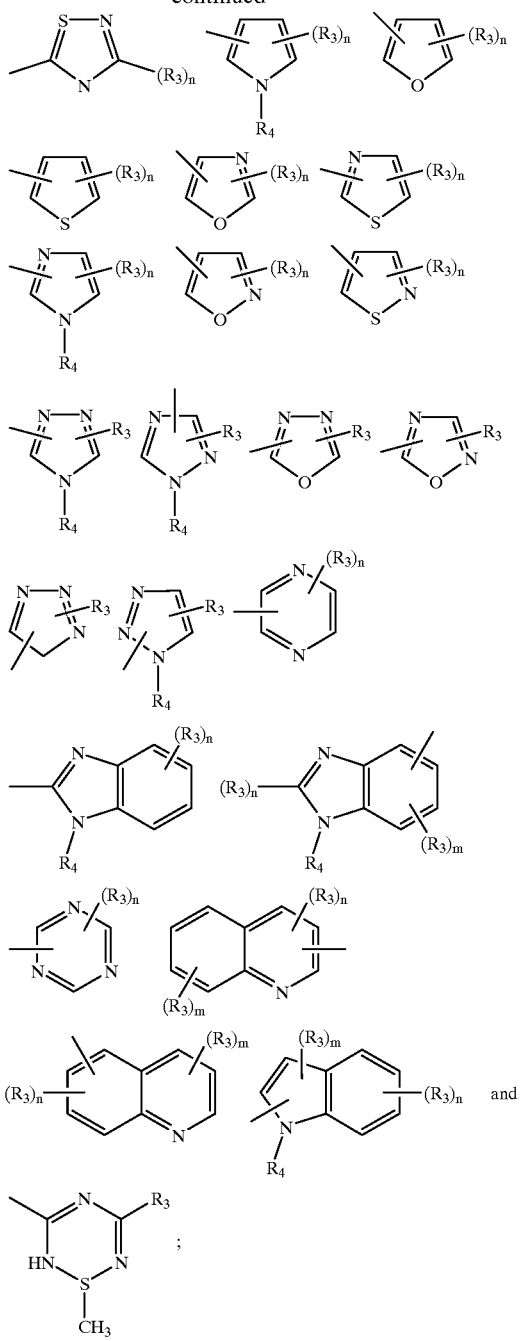

especially phenyl, naphthyl, pyridyl or thiadiazolyl; very especially phenyl or pyridyl; in particular phenyl;

$R_3$ is halogen, —CN, $NO_2$, halo-$C_1$-$C_2$alkyl, $C_1$-$C_2$alkoxy or halo-$C_1$-$C_2$alkoxy, halo-$C_2$-$C_5$alkenoxy or halo-$C_2$-$C_5$alkynyloxy; especially chlorine, —CN, $CF_3$ or $OCF_3$; where, if m+n is greater than 1, the radicals $R_3$ are independent of one another;

$R_4$ is H, $C_1$-$C_4$alkyl, phenyl or benzyl; especially H and methyl;

n is, depending on the possibilities for substitution on the ring system, 0 to 5, especially 1 to 4, more specifically 1 to 3, and the value of $n_1$ in $A_1$ is independent of the value of $n_2$ in $A_2$;

m, depending on the possibilities for substitution on the ring system, is 0 to 4, and the values of m in $A_1$ are independent of the values of m in $A_2$;

the total m+n in each radical $A_1$ and $A_2$ is 0 to 5; especially 1, 2, 3 or 4; more specifically 1 to 3, (2) a pesticidal composition comprising at least one compound of the formula (I) in which
$A_1$ and $A_2$ are phenyl;

(3) a pesticidal composition comprising at least one compound of the formula (I) in which
$R_1$ is —CN or halo-$C_1$-$C_2$alkyl; especially —CN or trifluoromethyl, more especially —CN;

(4) a pesticidal composition comprising at least one compound of the formula (I) in which
$R_2$ is hydrogen, $C_1$-$C_4$alkyl, $C_1$-$C_4$alkoxy-$C_1$-$C_4$alkyl, —C(=O)—$C_1$-$C_4$alkyl, —C(=O)-halo-$C_3$-$C_6$alkenyl, —C(=O)—$C_3$-$C_6$cycloalkyl, —C(=O)—O—$C_1$-$C_2$alkyl, —C(=O)—C(=O)—O—$C_1$-$C_2$alkyl, —C(=O)—C(=O)—N($R_6$)$_2$, cyano, benzoyl or benzyl, the benzoyl or benzyl radical being unsubstituted or mono- to trisubstituted in the aromatic ring by a substituent which is independent at each occurence and selected from the group consisting of halogen, —CN, —$NO_2$, trifluoromethoxy and trifluoromethyl; or —C(=O)—N($R_6$)$_2$; and the two radicals $R_6$ independently of one another are H, $C_1$-$C_4$alkyl, $C_3$-$C_6$cycloalkyl, phenyl or benzyl, the phenyl or benzyl group being unsubstituted or mono- or disubstituted in the aromatic ring by substituents which are independent of one another and selected from the group consisting of halogen, —CN, $C_1$-$C_4$alkyl, $C_1$-$C_4$alkoxy, halo-$C_1$-$C_2$alkyl and halo-$C_1$-$C_2$alkoxy; or two alkyl radicals $R_6$ together with the nitrogen atom to which they are bonded form a five- or six-membered ring in which a $CH_2$ group may be replaced by an O atom or by NH and in which the five- or six-membered ring is unsubstituted or mono- or disubstituted by methyl;

especially in which $R_2$ is hydrogen, $C_1$-$C_3$alkyl, $C_1$-$C_2$alkoxy-$C_1$-$C_2$alkyl, —C(=O)—$C_1$-$C_2$alkyl, —C(=O)-fluoro-$C_4$-$C_6$alkenyl, —C(=O)-cyclopropyl, —C(=O)—O—$C_1$-$C_2$alkyl, —C(=O)—C(=O)—O—$C_1$-$C_2$alkyl, —C(=O)—C(=O)—N($R_6$)$_2$, cyano, benzyl or o-nitrobenzyl; —C(=O)—N($R_6$)$_2$; or —C(=O)—$C_6H_5$ in which the phenyl ring is unsubstituted or mono- to trisubstituted by a substituent selected from the group consisting of halogen, $NO_2$, trifluoromethoxy and trifluoromethyl; and the two radicals $R_6$ independently of one another are H, $C_1$-$C_4$alkyl, cyclopropyl, phenyl or benzyl, the phenyl or benzyl group being unsubstituted or mono- or disubstituted in the aromatic ring by substituents which are independent of one another and selected from the group consisting of chlorine, —CN and $OCF_3$; or two alkyl radicals $R_6$ together with the nitrogen atom to which they are bonded form a six-membered ring in which a $CH_2$ group may be replaced by an O atom or by $NCH_3$;

(5) a pesticidal composition comprising at least one compound of the formula (I) in which
$A_1$ is a pyridyl radical;

(6) a pesticidal composition comprising at least one compound of the formula (I) in which
$(R_{3a})_{n1}$ is Cl, $Cl_2$, $Cl_3$, —$(CF_3)_2$, Cl—$CF_3$, $NO_2$, —CN, $Cl_2$—$NO_2$, —$OCF_3$, —$CF_3$, Cl—$CF_3$, $Cl_2$—$CF_3$, $Cl_3$—$OCF_3$, —$Cl_2$—F, $Cl_2$—Br, Cl—$CF_3$—F, Cl—Br—$CH_3$, —$(CH_3)_2$—Br, $Cl_3$—$CF_3$, $Cl_2$—F—$CF_3$, $F_2$—$CF_3$—Cl, $Cl_2$—CN, $Cl_2$—$CF_3$, $Cl_2$—$SCF_3$, $Cl_2$—$OCF_3$, $Cl_2$—$O_2CF_3$, $Cl_2$—$SO_2CH_3$, $Cl_2$—$OCF_2Br$, $Cl_2$—$OCF_2H$, $Cl_2$—$C_2F_5$, $(NO_2)_2$—$CF_3$, $(NO_2)_2$—Cl, $Cl_2$—$SO_2CH_3$ or $Cl_2$—$OSO2CF_3$; especially 2-Cl, 2,3-$Cl_2$, 2,4-$Cl_2$, 2,6-$Cl_2$, 2,4,6-$Cl_3$, 3,5-$(CF_3)_2$, 2-Cl-4-$CF_3$, 2-$NO_2$, 2-CN, 3-CN, 4-CN, 2,6-$Cl_2$-4-$NO_2$, 4-$OCF_3$, 4-$CF_3$, 3-$CF_3$, 2-Cl-4-$NO_2$, 2,6-$Cl_2$-4-$CF_3$, 2,6-$Cl_2$-4-$OCF_3$, 2,6-$Cl_2$-4-F, 2,6-$Cl_2$-4-Br, 2-Cl-4-$CF_3$-6-F, 2-Cl-4-Br-6-$CH_3$, 2,6-$(CH_3)_2$-4-Br, 2,3,6-$Cl_3$-4-$CF_3$, 2,6-$Cl_2$-3-F-4-$CF_3$, 2,3-$F_2$-4-$CF_3$-6-Cl, 2,6-$Cl_2$-4-CN, 2,4-$Cl_2$-6-$CF_3$, 2,6-$Cl_2$-4-$SCF_3$, 2,6-$Cl_2$-4-$SOCF_3$, 2,6-$Cl_2$-4-$SO_2CF_3$, 2,6-$Cl_2$-4-$SO_2CH_3$, 2,6-$Cl_2$-4-$OCF_2Br$, 2,6-$Cl_2$-4-$OCF_2H$, 2,6-$Cl_2$-4-$C_2F_5$, 2,6-$(NO_2)_2$-4-$CF_3$, 2,6-$(NO_2)_2$-4-Cl, 2,6-$Cl_2$-4-$OSO_2CH_3$, or 2,6-$Cl_2$-4-$OSO2CF_3$; very especially 2,3-$Cl_2$, 2,4-$Cl_2$, 2,6-$Cl_2$, 2,4,6-$Cl_3$, 3,5-$(CF_3)_2$, 2-Cl-4-$CF_3$, 2-CN, 3-CN, 4-CN, 2,6-$Cl_2$-4-$NO_2$, 4-$OCF_3$, 4-$CF_3$, 3-$CF_3$, 2-Cl-4-$NO_2$, 2,6-$Cl_2$-4-$CF_3$, 2,6-$Cl_2$-4-$OCF_3$, 2,6-$Cl_2$-4-F, 2,6-$Cl_2$-4-Br, 2-Cl-4-$CF_3$-6-F, 2-Cl-4-Br-6-$CH_3$, 2,6-$(CH_3)_2$-4-Br, 2,3,6-$Cl_3$-4-$CF_3$, 2,6-$Cl_2$-3-F-4-$CF_3$, 2,3-$F_2$-4-$CF_3$-6-Cl, 2,6-$Cl_2$-4—CN, 2,4-$Cl_2$-6-$CF_3$, 2,6-$Cl_2$-4-$SCF_3$, 2,6-$Cl_2$-4-$SOCF_3$, 2,6-$Cl_2$-4-$C_2F_5$, 2,6-$(NO_2)_2$-4-$CF_3$, 2,6-$(NO_2)_2$-4-Cl, 2,6-$Cl_2$-4-$OSO_2CH_3$, or 2,6-$Cl_2$-4-$OSO2CF_3$;

(7) a pesticidal composition comprising at least one compound of the formula (I) in which $(R_{3b})_{n2}$ is —CN, Cl, $Cl_2$, F, $F_2$, Br, —$NO_2$, —$(NO_2)_2$, —$NO_2$—$CF_3$, $CF_3$, —$(CF_3)_2$, —CN—$CF_3$, Cl—$CF_3$, F—CN, —Cl—CN, —$OCF_3$, —Cl—$NO_2$, —$CH_3$—$NO_2$, —$OCH_3$—$NO_2$, —$C_6H_5$, —$C_6H_4$—F, —$C_6H_4$—Cl, —$C_6H_4$—$CF_3$, —$C_6H_4$—$CF_3$, —$C_6H_4$—$NO_2$, —$C_6H_3$—$(CF_3)_2$, —$C_6H_3$—$Cl_2$, —$C_6H_3$—(Cl—F), —F—CN, F—$NO_2$, —CHO or —C(=O)$CF_3$; especially 4—CN, 3-CN, 4-$Cl_2$, 3,4-$Cl_2$, 2,3-$Cl_2$, 3,5-$Cl_2$, 2,5-$Cl_2$, 3,5-$F_2$, 2,6-$F_2$, 4-Br, 2-F, 4-$NO_2$, 2-$NO_2$-4-$CF_3$, 3-$CF_3$, 4-$CF_3$, 3,5-$(CF_3)_2$, 2-CN-4-$CF_3$, 2-Cl-4-$CF_3$, 2-F-4-CN, 3-Cl-4-CN, 4-$OCF_3$, 3-$OCF_3$, 4-Cl-3-$NO_2$, 2-Cl-4-$NO_2$, 3-$CH_3$-4-$NO_2$, 3-$OCH_3$-4-$NO_2$, 4-$C_6H_5$, 4-$C_6H_4$-4-F, 4-$C_6H_4$-4-Cl, 4-$C_6H_4$-4-$CF_3$, 4-$C_6H_4$-3-$CF_3$, 4-$C_6H_4$-3-$NO_2$, 4-$C_6H_3$-(3,5-$CF_3)_2$, 4-$C_6H_3$-2,4-$Cl_2$, 4-$C_6H_3$-3,4-$Cl_2$, 4-$C_6H_3$-3,5-$Cl_2$, 4-$C_6H_3$-(3-Cl-4-F), 2-F-4-$NO_2$, 4-CHO or 4-C(=O)$CF_3$; very especially 4-$NO_2$, 4-CN, 3-CN, 4-Cl, 3,4-$Cl_2$, 2,3-$Cl_2$, 3,5-$Cl_2$, 2,5-$Cl_2$, 3,5-$F_2$, 2,6-$F_2$, 2-F, 2-$NO_2$-4-$CF_3$, 3-$CF_3$, 4-$CF_3$, 3,5-$(CF_3)_2$, 2-CN-4-$CF_3$, 2-Cl-4-$CF_3$, 2-F-4-CN, 3-Cl-4-CN, 4-$OCF_3$, 3-$OCF_3$, 4-Cl-3-$NO_2$, 2-Cl-4-$NO_2$, 3-$CH_3$-4-$NO_2$, 3-$OCH_3$-4-$NO_2$, 4-$C_6H_5$, 2-F-4-$NO_2$, 4-CHO or 4-C(=O)$CF_3$.

(8) a pesticidal composition comprising at least one compound of the formula (I) in which $(R_{3a})_{n1}$ is 2-Cl, 2,3-$Cl_2$, 2,4-$Cl_2$, 2,6-$Cl_2$, 2,4,6-$Cl_3$, 3,5-$(CF_3)_2$, 2-Cl-4-$CF_3$, 4-$NO_2$, 2-$NO_2$, 2-CN, 3-CN, 4-CN, 2,6-$Cl_2$-4-$NO_2$, 4-$OCF_3$, 4-$CF_3$, 3-$CF_3$, 2-Cl-4-$NO_2$, 2,6-$Cl_2$-4-$CF_3$, 2,6-$Cl_2$-4-$OCF_3$, 2,6-$Cl_2$-4-F, 2,6-$Cl_2$-4-Br, 2-Cl-4-$CF_3$-6-F, 2-Cl-4-Br-6-$Ch_3$, 2,6-$(CH_3)_2$-4-Br, 2,3,6-$Cl_3$-4-$CF_3$, 2,6-$Cl_2$-3-F-4-$CF_3$, 2,3-$F_2$-$CF_3$-6-Cl, 2,6-$Cl_2$-4-CN, 2,4-$Cl_2$-6-$CF_3$, 2,6-$Cl_2$-4-$SCF_3$, 2,6-$Cl_2$-4-$SOCF_3$, 2,6-$Cl_2$-4-$SO_2CF_3$, 2,6-$Cl_2$-4-$SO_2CH_3$, 2,6-$Cl_2$-4-$OCF_2Br$, 2,6-$Cl_2$-4-$OCF_2H$, 2,6-$Cl_2$-4-$C_2F_5$, 2,6-$(NO_2)_2$-4-$CF_3$, 2,6-$(NO_2)_2$-4-Cl, 2,6-$Cl_2$-4-$OSO_2CH_3$, or 2,6-$Cl_2$-4-$OSO2CF_3$; and $(R_{3b})_{n2}$ is 4-CN, 3-CN, 4-Cl, 3,4-$Cl_2$, 2,3-$Cl_2$, 3,5-$Cl_2$, 2,5-$Cl_2$, 3,5-$F_2$, 2,6-$F_2$, 4-Br, 2-F, 4-$NO_2$, 2-$NO_2$, 2,4-$(NO_2)_2$, 2-$NO_2$-4-$CF_3$, 3-$CF_3$, 4-$CF_3$, 3,5-$(CF_3)_2$, 2-CN-4-$CF_3$, 2-Cl-4-$CF_3$, 2-F-4-CN, 3-Cl-4-CN, 4-$OCF_3$, 3-$OCF_3$, 4-Cl-3-$NO_2$, 2-Cl-4-$NO_2$, 3-$Ch_3$-4-$NO_2$, 3-$OCH_3$-4-$NO_2$, 4-$C_6H_5$, 4-$C_6H_4$-4-F, 4-$C_6H_4$-4-Cl, 4-$C_6H_4$-4-$CF_3$, 4-$C_6H_4$-3-$CF_3$, 4-$C_6H_4$-3-$NO_2$, 4-$C_6H_3$-(3,5-$CF_3)_2$, 4-$C_6H_3$-2,4-$Cl_2$, 4-$C_6H_3$-3,4-$Cl_2$, 4-$C_6H_3$-3,5-$Cl_2$, 4-$C_6H_3$-(3-Cl-4-F), 2-F-4-$NO_2$, 4-CHO or 4-C(=O)$CF_3$; very especially $(R_{3a})_{n1}$ is 2,3-$Cl_2$, 2,4-$Cl_2$, 2,6-$Cl_2$, 2,4,6-$Cl_3$, 3,5-$(CF_3)_2$, 2-Cl-4-$CF_3$, 2-CN, 3-CN, 4-CN, 2,6-$Cl_2$-4-$NO_2$, 4-$OCF_3$, 4-$CF_3$, 3-$CF_3$, 2-Cl-4-$NO_2$, 2,6-$Cl_2$-4-$CF_3$, 2,6-$Cl_2$-4-$OCF_3$, 2,6-$Cl_2$-4-F, 2,6-$Cl_2$-4-Br, 2-Cl-4-$CF_3$-6-F, 2-Cl-4-Br-6-$CH_3$, 2,6-$(CH_3)_2$-4-Br, 2,3,6-$Cl_3$-4-$CF_3$, 2,6-$Cl_2$-3-F-4-$CF_3$, 2,3-$F_2$-4-$CF_3$-6-Cl, 2,6-$Cl_2$-4-CN, 2,4-$Cl_2$-6-$CF_3$, 2,6-$Cl_2$-4-$SCF_3$, 2,6-$Cl_2$-4-$SOCF_3$, 2,6-$Cl_2$-4-$C_2F_5$, 2,6-$(NO_2)_2$-4-$CF_3$, 2,6-$(NO_2)_2$-4-Cl, 2,6-$Cl_2$-4-$OSO_2CH_3$, or 2,6-$Cl_2$-4-$OSO2CF_3$; and $(R_{3b})_{n2}$ is 4-CN, 3-CN, 4-Cl, 3,4-$Cl_2$, 2,3-$Cl_2$, 3,5-$Cl_2$, 2,5-$Cl_2$, 3,5-$F_2$, 2,6-$F_2$, 2-F, 4-$NO_2$, 2-$NO_2$-4-$CF_3$, 3-$CF_3$, 4-$CF_3$, 3,5-$(CF_3)_2$, 2-CN-4-$CF_3$, 2-Cl-4-$CF_3$, 2-F-4-CN, 3-Cl-4-CN, 4-$OCF_3$, 3-$OCF_3$, 4-Cl-3-$NO_2$, 2-Cl-4-$NO_2$, 3-$CH_3$-4-$NO_2$, 3-$OCH_3$-4-$NO_2$, 4-$C_6H_5$, 2-F-4-$NO_2$, 4-CHO or 4-C(=O)$CF_3$;

(9) a pesticidal composition comprising at least one compound of the formula (I) in which $R_2$ is hydrogen;

(10) a pesticidal composition comprising at least one compound of the formula (I) in which $R_2$ is —OH, $C_1$–$C_6$alkyl, $C_1$–$C_6$alkoxy, $C_3$–$C_6$cycloalkyl, $C_3$–$C_6$alkenyl, $C_3$–$C_6$alkynyl, halo-$C_3$–$C_6$alkenyl, benzyl or benzoyl, the benzyl or benzoyl radical being unsubstituted or mono- to trisubstituted in the aromatic ring by substituents which are independent of one another and selected from the group consisting of halogen, —CN, $NO_2$, $C_1$–$C_6$alkyl, $C_1$–$C_6$alkoxy, halo-$C_1$–$C_6$alkyl and halo-$C_1$–$C_6$alkoxy; $C_1$–$C_6$alkoxy-$C_1$–$C_6$alkyl, cyano-$C_1$–$C_6$alkyl, —C(=X)—$R_7$, —OC(=O)—$R_7$, —C(=O)—C(=O)—$R_7$, —S(=O)$_p$N($R_6)_2$ (in which the two $R_6$ are independent of one another); cyano, —$CH_2$—N($R_5$)—C(=O)—$R_8$, —$CH_2$—S—C(=S)—$R_8$, —$C_1$–$C_4$alkyl-S(=O)$_p$—$R_9$, —S(=O)$_p$—$R_9$, or —$CH_2$—N($R_{10}$)—$SO_2$—$R_9$; especially —$CH_3$, —$C_2H_5$, n-$C_3H_7$, i-$C_3H_7$, —$CH_2OC_2H_5$, —$CH_2OCH_3$, —$CH_2$—S—$CH_3$, —CN, —$COCH_3$, —$CH_2$—CH=$CH_2$, —$CH_2$—CH=$CCl_2$, —$CH_2C$≡CH, —$CH_2C_6H_5$, —$CH_2C_6H_4$-2-$NO_2$, —$CH_2C_6H_4$-4-$NO_2$, —$CH_2C_6H_4$-2-$NO_2$,

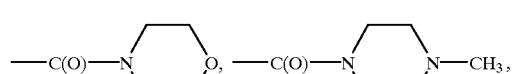

—$CH_2CN$, —$COC_2H_5$, —CO-cyclo-$C_3H_5$, —CO($CH_2$)$_3CH$=$CF_2$, —$CO_2CH_3$, —$CO_2C_2H_5$, —$CO_2C_2H_2CH(CH_3)_2$, —$CO_2C_8H_{17}$, —$CO_2C_2H_2CH(CH_3)_2$, —$CO_2C_6H_5$, —$CO_2CH_2C_6H_5$, —$CO_2CH_2CH_2Cl$, —$CH_2N(CH_3)CO_2C_2H_5$, —$CH_2N$—$CO_2C_2H_5$, —$CH_2N(CH_3)CO_2CH_3$, —$COCO_2CH_3$, —$COCO_2C_2H_5$, —$COCONHC_2H_5$, —$CONHCH_3$, —$CONHC_2H_5$, —$CONHC_6H_4$-4-$OCF_3$, —$COC_6H_4$-4-Cl, —$CH_2N(CH_3)SO_2CH_3$, —$CH_2N(CH_3)SO_2C_2H_5$, —$CH_2N(CH_3)SO_2C_6H_5$ or —$CH_2Cl$;

(11) a pesticidal composition comprising at least one compound of the formula (I) in which
  $n_1$ is 1, 2, 3 or 4, preferably 2 or 3;
(12) a pesticidal composition comprising at least one compound of the formula (I) in which
  $n_2$ is 1 or 2, preferably 1;
(13) a pesticidal composition comprising at least one compound of the formula (I) in which
  $n_1$ is 2, 3 or 4 and $n_2$ is 1 or 2;
(14) a pesticidal composition comprising at least one compound of the formula (I) in which
  $R_7$ is H, $C_1$–$C_6$alkyl, $C_3$–$C_6$alkenyl, halo-$C_1$–$C_6$alkyl, halo-$C_3$–$C_6$alkenyl, $C_1$–$C_6$alkoxy, halo-$C_1$–$C_6$alkoxy, $C_3$–$C_6$cycloalkyl, phenyl, benzyl, phenoxy, benzyloxy or —N($R_6$)$_2$ (in which the two $R_6$ are independent of one another).

Especially preferred within the scope of the invention are pesticides comprising at least one of the compounds of the formula (I) listed in Tables 3 to 29 and, where appropriate, the E/Z isomers and E/Z isomer mixtures thereof.

The invention furthermore relates to the compounds of the formula

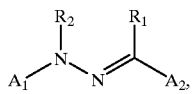

(Ia)

in which
$A_1$, $A_2$, $R_1$, $R_2$ and the substituents $R_{3a}$ and $R_{3b}$ of $A_1$ and $A_2$ have the meanings given hereinbefore for formula (I); and
$n_1$ and $n_2$ are, depending on the substitution options on the ring systems $A_1$ and $A_2$ in question, independently of each other, 1, 2, 3, 4 or 5; or, if appropriate, the E/Z isomers, E/Z isomer mixtures and/or tautomers thereof, in each case in free form or in salt form; with the proviso, that (P1) at least one of the substituents $R_{3a}$ and $R_{3b}$ is halogen-$C_1$–$C_6$-alkyl, halogen-$C_2$–$C_4$-alkenyl, halogen-$C_2$–$C_4$-alkinyl, halogen-$C_1$–$C_6$-alkoxy, $C_2$–$C_6$-alkenyloxy, $C_2$–$C_6$-alkynyloxy, halogen-$C_2$–$C_6$-alkenyloxy, halogen-$C_2$–$C_6$-alkynyloxy, —SF$_5$, —CHO, —C(=O)-halogen-$C_1$–$C_6$-alkyl, —C(=O)—O-halogen-$C_1$–$C_6$-alkyl, —O—C(=O)N($R_6$)$_2$ (in which the two $R_6$ are independent of one another); —CN, —S(=O)$_{2n}$($R_6$)$_2$ (in which the two $R_6$ are independent of one another); —S(=O)$_p$—$C_1$–$C_6$-alkyl, —S(=O)$_p$-halogen-$C_1$–$C_6$-alkyl, —O—S(=O)$_p$—$C_1$–$C_6$-alkyl, —O—S(=O)$_p$-halogen-$C_1$–$C_6$-Alkyl, phenyl, benzyl, phenoxy or benzyloxy, each of the phenyl, benzyl, phenoxy or benzyloxy radicals being unsubstituted or mono- to pentasubstituted in the aromatic ring by substituents which are independent of one another and selected from the group consisting of halogen, cyano, NO$_2$, $C_1$–$C_6$alkyl, halo-$C_1$–$C_6$alkyl, $C_1$–$C_6$alkoxy and halo-$C_1$–$C_6$alkoxy; when
  $n_1$ is 1 or 2; $n_2$ is 1; and $R_1$ is CN or halogen-$C_1$–$C_6$-alkyl, and $R_2$ is hydrogen;
  and with the further proviso, that
(P2) $R_{3a}$ is not 2-OH, when $A_2$ is 4-nitrophenyl; $R_1$ is CN; and $R_2$ is hydrogen;
  and with the further proviso, that
(P3) $A_1$ is not 4-chlorophenyl, 4-bromophenyl or 4-iodophenyl, when
  $A_2$ is 2,4-dinitrophenyl; $R_1$ is CN; and $R_2$ is hydrogen;
  and with the further proviso, that (P4) $A_1$ is not phenyl, when $A_2$ is tetrazolyl;
  $R_{3a}$ is 4-methyl, 4-methoxy, 4-Cl or 4-Br;
  $R_{3b}$ is monobromo-n-hexyl or monobromo-n-octyl;
  $n_1$ is 1; $R_1$ is CN; and $R_2$ is hydrogen;
  and with the further proviso, that
(P5) $A_1$ is not phenyl, when
  $A_2$ is imidazolyl; at least one $R_{3b}$ is CN;
  $R_1$ is CN; and $R_2$ is hydrogen;
  and with the further proviso, that
(P6) $A_1$ is not 3-nitrophenyl, when $A_2$ is a hetaryl radical;
  $R_1$ is —C(=S)NH$_2$ and $R_2$ is hydrogen;
  and with the further proviso, that
(P7) $A_1$ is not 4-nitrophenyl or 3,4-dinitrophenyl;
  and with the further proviso, that
(P8) $R_{3a}$ is not 2-nitro, when $A_1$ is phenyl and $n_1$ is 1, 2 or 3.

As far as the compounds of the formula (Ia) are concerned, the groups (1) to (14), which are mentioned hereinbefore as defining preferred groups of compounds of the formula (I) used as active ingredients in the compositions according to the invention, define also preferred groups of compounds of the formula (Ia), where, however, the provisos (P1) to (P8) mentioned hereinbefore have to be taken into consideration appropriately in each case.

The invention furthermore relates to a process for the preparation of the compounds of the formula (Ia) or, if appropriate, the E/Z isomers, E/Z isomer mixtures and/or tautomers thereof, in each case in free form or in salt form, which comprises, a) to prepare a compound of the formula (Ia) in which the radicals $R_1$, $A_1$ and $A_2$ have the same meanings as mentioned above and $R_2$ is hydrogen, and in which the same provisos (P1) to (P8) as mentioned above hold true, aa) diazotizing a compound of the formula

in which $A_1$ has the meanings mentioned above under formula (Ia), and ab) reacting the diazonium salt with a compound of the formula

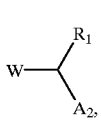

(IV)

in which $R_1$ and $A_2$ have the meanings mentioned above under formula (Ia) and W is hydrogen or a detachable group; or, b) to prepare a compound of the formula

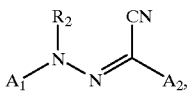

(I)

in which $A_1$, $A_2$ and $R_2$ have the meanings given above for compounds of the formula (Ia), and in which the same provisos (P1) to (P8) as mentioned above hold true
reacting a compound of the formula

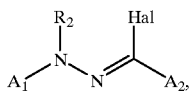
(II)

in which $A_1$, $A_2$ and $R_2$ have the meanings given above for the compounds of the formula (Ia) and Hal is a halogen atom, preferably chlorine or bromine, especially chlorine, with a metal cyanide, preferably an alkali metal cyanide, especially sodium cyanide; or, c) to prepare a compound of the formula (Ia) in which $R_2$ is other than H, reacting a compound of the formula (Ia) in which $R_2$ is hydrogen with a compound of the formula $R_2$—Q (V), in which $R_2$ has the meanings given above under formula (Ia) and Q is a leaving group, preferably chlorine, bromine or iodine, especially iodine, preferably in the presence of a base; or, d) to prepare a compound of the formula (Ia) in which $R_1$ is halo-$C_1$–$C_4$alkyl or —C(=S)—N($R_5$)$_2$, reacting a compound of the formula

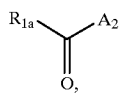
(VI)

in which $R_{1a}$ is halo-$C_1$–$C_4$alkyl or a group —C(=S)—N($R_5$)$_2$ and $A_2$ has the meanings defined for the compounds of the formula (Ia)
with a compound of the formula

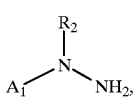
(VII)

in which $A_1$ and $R_2$ have the meanings given above for the compounds of the formula (Ia),
and in each case, if so desired, converting a compound of the formula (Ia) which can be obtained in accordance with the process or by any other means, or an E/Z isomer or tautomer thereof, in each case in free form or in salt form, into a different compound of the to formula (Ia) or into an E/Z isomer or tautomer thereof, in each case in tree form or in salt form, resolving an E/Z isomer mixture which can be obtained in accordance with the process and isolating the desired isomer and/or converting a free compound of the formula (Ia) which can be obtained in accordance with the process or by any other means, or an E/Z isomer or tautomer thereof, into a salt or converting a salt of a compound of the formula (I) which can be obtained in accordance with the process or by any other means, or an E/Z isomer or tautomer thereof, into the free compound of the formula (Ia) or an E/Z isomer or tautomer thereof or into another salt.

The invention furthermore relates to a process for the preparation of a compound of the formula (II), in which $A_1$, $A_2$ and $R_2$ have the meanings given above for the compounds of the formula (Ia) and Hal is a halogen atom, and, if appropriate, the E/Z isomers and tautomers thereof, in each case in free form or in salt form, which comprises
e) reacting a compound of the formula

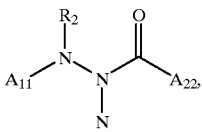
(VIII)

in which the radicals $A_{11}$, $A_{22}$ and $R_2$ have the same meaning as indicated above for $A_1$ and $A_2$ under formula (Ia), with a halogenating agent, or
f) reacting a compound of the formula

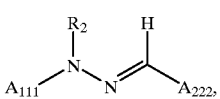
(IX)

in which $R_2$ and the two radicals $A_{111}$ and $A_{222}$ have the same meaning as given for $A_1$ and $A_2$ above under formula (Ia), with N-bromosuccinimide or N-chlorosuccinimide in the presence of a thioether;
and in each case, if so desired, converting a compound of the formula (II) which can be obtained in accordance with the process or by any other means, or an E/Z isomer or tautomer thereof, in each case in free form or in salt form, into a different compound of the formula (II) or into an E/Z isomer or tautomer thereof, in each case in free form or in salt form, resolving an E/Z isomer mixture which can be obtained in accordance with the process and isolating the desired isomer and/or converting a free compound of the formula (II) which can be obtained in accordance with the process or by any other means, or an E/Z isomer or tautomer thereof, into a salt or converting a salt of a compound of the formula (II) which can be obtained in accordance with the process or by any other means, or an E/Z isomer or tautomer thereof, into the free compound of the formula (II) or an E/Z isomer or tautomer thereof or into another salt.

The reactions described hereinabove and hereinbelow are carried out in a manner known per se, for example in the absence or, normally, in the presence of a suitable solvent or diluent or a mixture of these, the process being carried out, as required, with cooling, at room temperature or with heating, for example in a temperature range of from approximately 0° C. to the boiling point of the reaction medium, preferably from approximately 20° C. to approximately +120° C., in particular 60° C. to 80° C., and, if required, in a sealed vessel, under pressure, in an inert gas atmosphere and/or under anhydrous conditions. Especially advantageous reaction conditions can be seen from the examples.
Variant a)
aa) Diazotation is effected under the conditions known to those skilled in the art, that is to say in the presence of strong inorganic acids, such as mineral acids, e.g. perchloric acid, sulfuric acid, nitric acid, nitrous acid, phosphoric acid or a hydrohalic acid, normally in the presence of water, but also in pure sulfuric acid.

Depending on the basicity of the aromatic amine, the reaction is carried out in a temperature range of approximately −10° C. to approximately +20° C., or else, if required, at higher temperatures, for example at 60° C. to 80° C.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The reaction time is preferably approximately 1 to approximately 2 hours.

The product is normally not isolated, but processed immediately in the next reaction step.

Especially preferred conditions for the reaction are described in Example H6/a.

ab) The reaction is normally carried out in the presence of water and, preferably, in the presence of an organic carboxylic acid, e.g. formic acid, chloroacetic acid, trifluoroacetic acid, cyanoacetic acid. oxalic acid, malonic acid, succinic acid, maleic acid, fumaric acid or phthalic acid; it is especially preferred to add acetic acid.

A detachable group W is to be understood as meaning an electron-attracting group which is easily detachable under the reaction conditions which prevail. Particularly suitable for this purpose is a group —C(=O)R or —OC(=O)R in which R is H, $C_1$–$C_4$alkyl, halo-$C_1$–$C_4$alkyl, $C_1$–$C_4$alkoxy, halo-$C_1$–$C_4$alkoxy; —CN, or organic sulfonates, such as $C_1$–$C_4$alkane- or arylsulfonates which are unsubstituted or substituted, for example by halogen, e.g. methane-, trifluoromethane- or p-toluenesulfonate.

The reaction is advantageously carried out in a temperature range from approximately −10° C. to approximately +30° C., preferably from approximately 0° C. to approximately +25° C.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The reaction time is not critical; a reaction time of approximately 0.5 to approximately 8 hours, in particular from approximately 2 to approximately 4 hours, is preferred.

The product is isolated by customary methods, e.g. by filtration, crystallization, distillation or chromatography, or any suitable combination of these processes.

Especially preferred conditions for the reaction are described in Example H6/b.

Variant b)

Suitable for the reaction are transition metal cyanides, such as CuCN or $Ni(CN)_2$, and also alkaline earth metal and alkali metal cyanides; especially KCN and NaCN.

The reactants can be reacted with each other as such, i.e. without addition of a solvent or diluent, e.g. in the melt. In most cases, however, the addition of an inert solvent or diluent or a mixture of these is advantageous. Examples of such solvents or diluents which may be mentioned are: aromatic, aliphatic and alicyclic hydrocarbons and halohydrocarbons such as benzene. toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethane or tetrachloroethene; esters such as ethyl acetate; ethers such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones such as acetone, methyl ethyl ketone or methyl isobutyl ketone; alcohols such as methanol, ethanol, propanol, isopropanol, butanol, ethylene glycol or glycerol; amides such as N,N-dimethyliformamide, N,N-diethylformamide, N,N-dimethylacetamide, N-methylpyrrolidone or hexamethylphosphoric triamide; nitrites, such as acetonitrile or propionitrile; and sulfoxides such as dimethyl sulfoxide; or water. Preferred are alcohols and water, or alcohol/water mixtures.

The reaction is advantageously carried out in a temperature range from approximately 0° C. to approximately 80° C., preferably from approximately 20° C. to approximately 30° C., in many cases in the range between room temperature and the reflux temperature of the reaction mixture.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The reaction time is not critical; a reaction time of approximately 0.1 to approximately 24 hours, in particular from approximately 3 to approximately 5 hours, is preferred.

The product is isolated by customary methods, e.g. by filtration, crystallization, distillation or chromatography, or any suitable combination of these processes.

In a preferred embodiment of variant b), a compound of the formula (II) is reacted with sodium cyanide in an ethanol/water mixture at room temperature. Especially preferred conditions for the reaction are described in Example H5.

Variant c)

Examples of suitable leaving groups Q in the compounds of the formula (V) are hydroxyl, $C_1$–$C_8$alkoxy. halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesultonyloxy, halo-$C_1$–$C_8$alkanesulfonyloxy, benzenesulfonyloxy, toluenesulfonyloxy and halogen, preferably toluenesulfonyloxy, trifluoromethanesulfonyloxy or halogen, in particular halogen, especially chlorine, bromine or iodine, especially iodine.

Examples of suitable bases for facilitating the reaction are the hydroxides, hydrides, amides, alkoxides, acetates, carbonates, dialkylamides or alkylsilylamides of alkali metals or alkaline earth metals, or alkylamines, alkylenediamines, free or N-alkylated, saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide, and 1,5-diazabicyclo[5.4.0]undec-5-ene (DBU). Alkali metal carbonates, alkaline earth metal carbonates, alkylamines, alkali metal alkoxides and alkaline earth metal alkoxides are preferred.

The reactants can be reacted with each other as such, i.e. without addition of a solvent or diluent, e.g. in the melt. In most cases, however, it is advantageous to add an inert solvent or diluent or mixture of these. Examples of such solvents or diluents which may be mentioned are: aromatic, aliphatic and alicyclic hydrocarbons such as benzene, toluene, xylene, mesitylene, tetralin, chlorobenzene, dichlorobenzene, bromobenzene, petroleum ether, hexane, cyclohexane; ethers such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters such as ethyl acetate and methyl acetate; and sulfoxides such as dimethyl sulfoxide. Preferred are ethers, for example tert-butyl methyl ether, tetrahydrofuran or dioxane, and esters, for example ethyl acetate.

The reaction is advantageously carried out in a temperature range from approximately 0° C. to approximately +120° C., preferably from approximately 0° C. to approximately +80° C.

The reaction is preferably carried out under atmospheric pressure.

The reaction time is not critical; a reaction time of from approximately 0.1 to approximately 24 hours, in particular of from approximately 0.5 to approximately 2 hours, is preferred.

The product is isolated by customary methods, e.g. by filtration, crystallization, distillation or chromatography, or any suitable combination of these processes.

Especially preferred conditions for the reaction are described in Examples H7 and H8.

Variant d)

The reaction is preferably carried out in the presence of an acidic catalyst, for example in the presence of a carboxylic acid such as formic acid, acetic acid, malonic acid or oxalic acid, or else of a sulfonic acid such as $C_1$–$C_4$alkane- or arylsulfonic acid which is unsubstituted or substituted, for example by halogen, e.g. methane-, trifluoromethane- or p-toluenesulfonic acid.

The reactants can be reacted with each other as such, i.e. without addition of a solvent or diluent, for example in the melt. In most cases, however, it is advantageous to add an inert solvent or diluent or a mixture of these. Particularly suitable are solvents which are suitable for the azeotropic removal of water. Examples of such solvents or diluents which may be mentioned are: aromatic, aliphatic and alicyclic hydrocarbons and halohydrocarbons such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters such as ethyl acetate; ethers such as dipropyl ether, diisopropyl ether, dibutyl ether, tert-butyl methyl ether, dimethoxydiethyl ether; ketones such as methyl isobutyl ketone; alcohols such as ethanol, propanol, isopropanol, butanol, ethylene glycol or glycerol.

The reaction is advantageously carried out in a temperature range from approximately 60° C. to approximately 180° C., preferably from approximately 80° C. to approximately 130° C., in many cases at the reflux temperature of the reaction mixture.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The preferred reaction time is approximately 6 to approximately 72 hours, in particular from approximately 12 to approximately 48 hours.

The product is isolated by customary methods, e.g. by filtration, crystallization, distillation or chromatography, or any suitable combination of these processes.

In a preferred embodiment of variant d), the reaction is carried out at 80° C. to 140° C. in an alcohol or an aromatic hydrocarbon in the presence of a $C_1$–$C_4$carboxylic acid.

Especially preferred conditions for the reaction are described in Example H10.

Variant e)

Preferred halogenating agents are $Cl_2$, $Br_2$, SOCl2, $SO_2Cl_2$, $POCl_3$, $PCl_3$, $PCl_5$ and $COCL_2$.

The reactants can be reacted with each other as such, i.e. without addition of a solvent or diluent, for example in the melt. In most cases, however, it is advantageous to add an inert solvent or diluent or a mixture of these. Examples of such solvents or diluents which may be mentioned are: aromatic, aliphatic and alicyclic hydrocarbons and halohydrocarbons such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; esters such as ethyl acetate; ethers such as diethyl ether, dipropyl ether, diisopropyl ether, dibutyl ether, tert-butyl methyl ether, ethylene glycol dimethyl ether, dimethoxydiethyl ether, tetrahydrofuran or dioxane; ketones such as acetone, methyl ethyl ketone or methyl isobutyl ketone; amides such as N,N-dimethylformamide, N,N-diethylformamide, N,N-dimethylacetamide, N-methylpyrrolidone or hexamethylphosphoric triamide; and nitrites such as acetonitrile or propionitrile.

The reaction is advantageously carried out in a temperature range from approximately 0° C. to approximately 180° C., preferably from approximately 50° C. to approximately 100° C., in many cases in the range between room temperature and the reflux temperature of the reaction mixture.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The reaction time is not critical; preferred is a reaction time of from approximately 0.1 to approximately 24 hours, in particular from approximately 3 to approximately 6 hours.

The product is isolated by customary methods, e.g. by filtration, crystallization, distillation or chromatography. or any suitable combination of these processes.

Especially preferred conditions for the reaction are described in Example H3.

Variant f)

The reactants can be reacted with each other as such, i.e. without addition of a solvent or diluent, for example in the melt. In most cases, however, it is advantageous to add an inert solvent or diluent or a mixture of these. Examples of such solvents or diluents which may be mentioned are: aromatic, aliphatic and alicyclic hydrocarbons and halohydrocarbons such as benzene, toluene. xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers such as diethyl ether, dipropyl ether, diisopropyl ether, dibutyl ether, tertbutyl methyl ether, ethylene glycol dimethyl ether, dimethoxydiethyl ether, tetrahydrofuran or dioxane; and nitrites such as acetonitrile or propionitrile.

Thioethers which are preferably added are dialkyl thioethers, especially diethyl sulfide or dimethyl sulfide, preferably dimethyl sulfide.

The reaction is advantageously carried out in a temperature range of from approximately 0° C. to approximately −100° C., especially at −50 to −80° C., preferably at approximately −60° C.

The reaction is preferably carried out under atmospheric pressure.

The reaction can be carried out without a protective gas atmosphere; however, it is preferably carried out under a protective gas atmosphere, e.g. nitrogen or argon, in particular nitrogen.

The reaction time is not critical; preferred is a reaction time of from approximately 0.1 to approximately 24 hours, in particular from approximately 3 to approximately 6 hours.

The product is isolated by customary methods, e.g. by filtration, crystallization, distillation or chromatography, or any suitable combination of these processes.

The compounds of the formulae (I), (II) and (VIII) can be in the form of one of the isomers which are possible or as a mixture of these, for example depending on the number, absolute and relative configuration of the asymmetric carbon atoms, as pure isomers such as antipodes and/or diastereomers, or as isomer mixtures, such as enantiomer mixtures, for example racemates, diastereomer mixtures or racemate mixtures; the invention relates to the pure isomers and also to all isomer mixtures which are possible and is to be understood hereinabove and hereinbelow in each case in this sense even when stereochemical details are not mentioned specifically in each case.

Diastereomer mixtures and racemate mixtures of compounds of the formulae (I), (II) and (VIII) which can be obtained in accordance with the process—depending on the choice of starting materials and procedures—or by other means can be resolved into the pure diastereomers or racemates in the known manner on the basis of the physicochemical differences of the components, for example by fractional crystallization, distillation and/or chromatography.

Enantiomer mixtures which can be obtained accordingly, such as racemates, can be separated into the optical antipodes by customary methods, for example by recrystallization from an optically active solvent, by chromatography on chiral adsorbents, for example high-performance liquid chromatography (HPLC) on acetylcellulose, with the aid of suitable microorganisms, by cleavage with specific immobilized enzymes, via the formation of inclusion compounds, for example using chiral crown ethers, where only one enantiomer is complexed.

In addition to separating appropriate isomer mixtures, pure diastereomers or enantiomers can also be obtained in accordance with the invention by generally known methods of diastereoselective or enantioselective synthesis, for example by carrying out the process according to the invention with starting materials of a suitable stereochemistry.

It is advantageous to isolate, or synthesize, in each case the biologically more effective isomer, for example enantiomer, or isomer mixture, for example enantiomer mixture, if the individual components have different biological activity.

The compounds of the formulae (I), (II) and (VIII) can also be obtained in the form of their hydrates and/or include other solvents, for example, if desired, those which have been used for crystallizing compounds in solid form.

The invention relates to all those embodiments of the process which start from a compound which can be obtained as starting material or intermediate at any level of the process and where all or some of the missing steps are carried out or where a starting material is used in the form of a derivative or salt and/or the racemates or antipodes thereof or, in particular, such a starting material is formed under the reaction conditions.

Starting materials and intermediates which are preferably used in the process of the present invention are those which lead to the compounds of the formula (I) which have been described at the outset as being particularly valuable.

In particular, the invention relates to the preparation processes described in Examples H5, H6, H7, H8 and H10.

The invention also relates to starting materials and intermediates used for the preparation of the compounds of the formula (I), in particular to those compounds of the formulae (II) and (VIII), which are novel, and to their use and processes for their preparation. The compounds of the formulae II and VIII, in particular, can be prepared analogously to Examples H1 and H3, respectively.

Those compounds of the formulae (III) to (VII) and (IX) which are not already known can be prepared by processes known per se.

The invention furthermore relates to a method of controlling pests using a compound of the formula (I), in which $A_1$, $A_2$, $R_1$ and $R_2$ are as indicated above for formula (I), with the exception of 1-phenylhydrazono-2-nitriloethylbenzene.

The compounds of the formula (I) according to the invention are preventively and/or curatively valuable active ingredients in the field of pest control, even at low rates of concentration, which have a very favourable biocide spectrum and are well tolerated by warm-blooded species, fish and plants. The term pests first of all includes in the frame of the present invention insects, representatives of the order Acarina, microorganisms, and representatives of the classes Nematoda and Trematoda; especially insects, representatives of the order Acarina and phytopathogenic fungi, more particularly insects and representatives of the order Acarina. The active ingredients according to the invention are effective against all or individual developmental stages of normally sensitive, but also resistant, animal pests such as insects and representatives of the order Acarina. The insecticidal, ovicidal and/or acaricidal activity of the active ingredients according to the invention can manifest itself directly, i.e. in mortality of the pests, which takes place immediately or only after some time has elapsed, for example during ecdysis, or of their eggs, or indirectly, for example in a reduced oviposition rate and/or hatching rate, the good activity corresponding to a mortality rate (mortality) of at least 50 to 60%.

Examples of the abovementioned animal pests are:

from the order Lepidoptera, for example,

Acleris spp., Adoxophyes spp., Aegeria spp., Agrotis spp., *Alabama argillaceae,* Amylois spp., *Anticarsia gemmatalis,* Archips spp., Argyrotaenia spp., Autographa spp., *Busseola fusca, Cadra cautella, Carposina nipponensis,* Chilo spp., Choristoneura spp., *Clysia ambiguelta,* Cnaphalocrocis spp., Cnephasia spp., Cochylis spp., Coleophora spp., *Crocidolomia binotalis, Cryptophlebia leucotreta,* Cydia spp., Diatraea spp., *Diparopsis castanea,* Earias spp., Ephestia spp., Eucosma spp., *Eupoecilia ambiguella,* Euproctis spp., Euxoa spp., Grapholita spp., *Hedya nubiferana,* Heliothis spp., *Hellula undalis, Hyphantria cunea, Keiferia lycopersicella, Leucoptera scitella,* Lithocollethis spp., *Lobesia botrana,* Lymantria spp., Lyonetia spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,*

Pieris spp., *Plutella xylostella,* Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example,

Agriotes spp., Anthonomus spp., *Atomaria linearis, Chaetocnema tibialis,* Cosmopolites spp., Curculio spp., Dermestes spp., Diabrotica spp., Epilachna spp., Eremnus spp., *Leptinotarsa decemlineata,* Lissorhoptrus spp., Meiolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example,

Blatta spp., Blattella spp., Gryllotalpa spp., *Leucophaea maderae,* Locusta spp., Periplaneta spp. and Schistocerca spp.;

from the order Isoptera, for example, Reticulitermes spp.;

from the order Psocoptera, for example, Liposcelis spp.;

from the order Anoplura, for example, Haematopinus spp., Linognathus spp., Pediculus spp., Pemphigus spp. and Phylloxera spp.;

from the order Mallophaga, for example, Damalinea spp. and Trichodectes spp.;

from the order Thysanoptera, for example, Frankliniella spp., Hercinothrips spp., Taeniothrips spp., *Thrips palmi, Thrips tabaci* and *Scirtothrips aurantii;* from the order Heteroptera, for example, Cimex spp., *Distantiella theobroma,* Dysdercus spp., Euchistus spp. Eurygaster spp. Leptocorisa spp., Nezara spp., Piesma spp., Rhodnius spp., *Sahlbergella singularis,* Scotinophara spp. and Triatoma spp.;

from the order Homoptera, for example, *Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylia spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example, Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

from the order Diptera, for example, Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.;

from the order Siphonaptera, for example, *Ctenocephalides felis, Ctenocephalides canis,* Ceratophyllus spp. and *Xenopsylla cheopis;* from the order Thysanura, for example, *Lepisma saccharina* and from the order Acarina, for example, *Acarus siro, Aceria sheldoni, Aculus schlechtendali,* Amblyomma spp., Argas spp., Boophilus spp., Brevipaipus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.

From the class Trematoda especially representatives of the family Fasciolidae, especially *Fasciola hepatica:* and from of the class Nematoda for example the families Filariidae and Setariidae, especially the genera Haemonchus, Trichostrongylus, Ostertagia, Nematodirus, Cooperia, Ascaris, Bunostomum, Oesophagostomum, Chabertia, Trichuris, especially *Trichuris vulpis,* Strongylus, Trichonema, Dictyocaulus, Capillaria, Strongyloides, Heterakis, Toxocara, especially *Toxocara canis,* Ascaridia, Oxyuris, Ancylostoma, especially *Ancylostoma caninum,* Uncinaria, Toxascaris and Parascaris; Dirofilaria, especially *Dirofilaria immitis* (heart worm).

The activity of the compositions comprising the compounds of the formula (I) and of the compounds of the formula (Ia) can be substantially broadened and adapted to prevailing circumstances by the addition of other insecticides and/or acaricides. Examples of suitable additional active ingredients include representatives of the following classes of compounds: Thioureas, benzoylureas, carbamoyloximes, halogated carboxylic acid derivatives, organophosphates, organochloro derivatives, nitroenamines, nitroguanidines, cyanoguanidines, carbamates, thiocarbamates, carbodiimides, formamidines, benzilic acid derivatives, dioxolanes, thiadiazinderivatives, unsymmetrical triazines, symmetrical triazines, pyridazinones, pyrroles, phenoxyphenylethers, sulfonic acid amides, *Bacillus thuringiensis*-preparations, milbemycines, avermectines and pyrethroids.

The active ingredients according to the invention can be used for controlling, i.e. containing or destroying, pests of the abovementioned type in particular on plants, mainly on crops of useful plants and ornamentals in agriculture, in horticulture and in silviculture, or on parts of such plants, such as fruits, flowers, foliage, stalks, tubers or roots, and in some cases even parts of plants which are formed at a later point in time are afforded protection against these pests Target crops which are suitable are, in particular, cereals, such as wheat, barley, rye, oats, rice, maize or sorghum; beet, such as sugar or fodder beet; fruit, e.g. pomaceous fruit, stone fruit and soft fruit, such as apples, pears, plums, peaches, almonds, cherries or berries, for example strawberries, raspberries or blackberries; leguminous plants, such as beans, lentils, peas or soya; oil crops, such as oilseed rape, mustard, poppies, olives, sunflowers, coconut, castor, cocoa or groundnuts; cucurbits, such as pumpkins, cucumbers or melons; fibre plants, such as cotton, flax, hemp or jute; citrus fruit, such as oranges, lemons, grapefruits or tangerines; vegetables, such as spinach, lettuce, asparagus, cabbages, carrots, onions, tomatoes, potatoes or bell peppers; the laurel family, such as avocado, Cinnamonium, or camphor; and also tobacco, nuts, coffee, egg plants, sugar cane, tea, pepper, grapevines, hops, the plantain family, latex plants and ornamentals.

The active ingredients according to the invention are especially suitable for controlling insects and representatives of the order Acarina, in particular feeding insects which damage plants, such as *Anthonomus grandis, Diabrotica balteata, Heliothis virescens* larvae, *Plutella xylostella* and *Spodoptera littoralis* larvae, and spider mites such as Tetranychus spp. in cotton, fruit, maize, soya, oilseed rape and vegetable crops.

Other fields of application of the active ingredients according to the invention are the protection of stored products and stores and of material, and, in the hygiene sector, in particular the protection of domestic animals or productive livestock against pests of the abovementioned type.

The invention therefore especially relates to a pesticidal composition which comprises a compound of the formula (I), with the exception of 1-phenylhydrazono-2-nitriloethylbenzene, in the form of emulsifiable concentrates, suspension concentrates, directly sprayable or dilutable solutions, spreadable pastes, dilute emulsions, wettable powders, soluble powders, dispersible powders, wettable powders, dusts, granules or encapsulations in polymeric substances, all of which comprise—at least—one of the active ingredients according to the invention and which are to be selected to suit the intended aims and prevailing circumstances.

In these compositions, the active ingredient is employed together with—at least—one of the auxiliaries conventionally used in the art of formulation, such as extenders, e.g. solvents or solid carriers, or such as surface-active compounds (surfactants).

Examples of suitable solvents are: non-hydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons such as paraffins or cyclohexane, alcohols such as ethanol, propano) or butanol, glycols and their ethers and esters such as propylene glycol, dipropylene glycol ether, ethylene glycol, ethylene glycol monomethyl ether or ethylene glycol monoethyl ether, ketones such as cyclohexanone, isophorone or diacetone alcohol, strongly polar solvents such as N-methylpyrrolid-2-one, dimethyl sulfoxide or N,N-dimethylformamide, water, free or epoxidized rapeseed, castor, coconut or soya oil, and silicone oils.

Solid carriers which are used for example for dusts and dispersible powders are, as a rule, ground natural minerals, such as calcite, talc, kaolin, montmorillonite or attapulgite. To improve the physical properties, it is also possible to add highly-disperse silicas or highly-disperse absorptive polymers. Suitable particulate adsorptive carriers for granules are porous types, such as pumice, brick grit, sepiolite or bentonite, and suitable non-sorptive carrier materials are calcite or sand. Moreover, a large number of granulated materials of inorganic or organic nature can be used, in particular dolomite or comminuted plant residues.

Suitable surface-active compounds are, depending on the nature of the active ingredient to be formulated, non-ionic, cationic and/or anionic surfactants or surfactant mixtures which have good emulsifying, dispersing and wetting properties. The surfactants listed below are only to be considered as examples; many more surfactants conventionally used in the art of formulation and suitable in accordance with the invention are described in the relevant literature.

Suitable non-ionic surfactants are primarily polyglycol ether derivatives of aliphatic or cycloaliphatic alcohols, of saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenots. Also suitable are water-soluble polyethylene oxide adducts with polypropylene glycol, ethylenediaminopolypropylene glycol and alkylpolypropylene glycol having 1 to 10 carbons in the alkyl chain and 20 to 250 ethylene glycol ether and 10 to 100 propylene glycol ether groups. The above-mentioned compounds normally contain 1 to 5 ethylene glycol units per propylene glycol unit. Examples which may be mentioned are nonylphenylpolyethoxyethanols, castor oil polyglycol ethers, polypropylene/polyethylene oxide adducts, tributylphenoxypolyethoxyethanol, polyethylene glycol and octylphenoxypoiyethoxyethanol. Also suitable are fatty acid esters of polyoxyethylene sorbitan, such as polyoxyethylene sorbitan trioleate.

The cationic surfactants are mainly quaternary ammonium salts which have, as substituents, at least one alkyl radical of 8 to 22 carbon atoms and, as further substituents, lower alkyl, benzyl or lower hydroxyalkyl radicals which may be halogenated. The salts are preferably in the form of halides, methylsulfates or ethylsulfates. Examples are stearyltrimethylammonium chloride and benzyldi(2-chloroethyl)ethylammonium bromide.

Suitable anionic surfactants can be both water-soluble soaps and water-soluble synthetic surface-active compounds. Soaps which are suitable are the alkali metal salts, alkaline earth metal salts and unsubstituted or substituted ammonium salts of higher fatty acids ($C_{10}$–$C_{22}$), such as the sodium or potassium salts of oleic or stearic acid, or of natural fatty acid mixtures which can be obtained, for example, from coconut or tall oil; mention must also be made of the fatty acid methyltaurinates. However, synthetic surfactants, in particular fatty sulfonates, fatty sulfates, sulfonated benzimidazole derivatives or alkylarylsulfonates, are used more frequently. As a rule, the fatty sulfonates and fatty sulfates exist as alkali metal salts, alkaline earth metal salts or unsubstituted or substituted ammonium salts and generally have an alkyl radical of 8 to 22 C atoms, alkyl also including the alkyl moiety of acyl radicals: examples which may be mentioned are the sodium or calcium salt of lignosulfonic acid, of the dodecylsulfuric ester or of a fatty alcohol sulfate mixture prepared with natural fatty acids. This group also includes the salts of the sulfuric esters and sulfonic acids of fatty alcohol/ethylene oxide adducts. The sulfonated benzimidazole derivatives preferably contain 2 sulfo groups and one fatty acid radical having approximately 8 to 22 C atoms. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensate. Also suitable are corresponding phosphates, such as salts of the phosphoric ester of a p-nonylphenol(4-14)ethylene oxide adduct, or phospholipids.

As a rule, the compositions comprise 0.0000001 to 99.99%, especially 0.1 to 99%, in particular 0.1 to 95%, of active ingredient and 0.01 to 99.9999999%, especially 1 to 99.9%, in particular 5 to 99.9%, of—at least—one solid or liquid auxiliary, it being possible, as a rule, for the surfactants to amount to 0 to 25%, in particular 0.1 to 20%, of the composition (% is in each case per cent by weight). While concentrated compositions are more preferred as commercially available goods, the end user uses, as a rule, dilute compositions, which have a considerably lower concentration of active ingredient. Preferred compositions are composed in particular as follows (%=percent by weight):

Emulsifiable concentrates:
  active ingredient: 1 to 90%, preferably 5 to 20%
  surfactant: 1 to 30%, preferably 10 to 20%
  solvent: 5 to 98%, preferably 70 to 85%
Dusts:
  active ingredient: 0.1 to 10%, preferably 0.1 to 1%
  solid carrier: 99.9 to 90%, preferably 99.9 to 99%
Suspension concentrates:
  active ingredient: 5 to 75%, preferably 10 to 50%
  water: 94 to 24%, preferably 88 to 30%
  surfactant: 1 to 40%, preferably 2 to 30%
Wettable powder:
  active ingredient: 0.5 to 90%, preferably 1 to 80%
  surfactant: 0.5 to 20%, preferably 1 to 15%
  solid carrier: 5 bis 99%, vorzugsweise 15 bis 98%
Granules:
  active ingredient: 0.5 to 30%, preferably 3 to 15%
  solid carrier: 99.5 to 70%, preferably 97 to 85%

The activity of the compositions according to the invention can be widened considerably, and adapted to prevailing circumstances, by adding other insecticidally, acaricidally and/or fungicidally active ingredients. Examples of suitable additives of active ingredients are representatives of the following classes of active ingredients: organophosphorus compounds, nitrophenols and derivatives, formamidines, ureas, carbamates, pyrethroids, chlorinated hydrocarbons and Bacillus thuringiensis peparations. The compositions according to the invention may also comprise other solid or liquid auxiliaries such as stabilizers, for example epoxidized or unepoxidized vegetable oils (e.g. epoxidized coconut oil, rapeseed oil or soya oil), antifoams, e.g. silicone oil, preservatives, viscosity regulators, binders and/or tackifiers, and also fertilizers or other active ingredients for achieving specific effects, for example bactericides, nematicides, molluscicides or selective herbicides.

The compositions according to the invention are prepared in a known manner, in the absence of auxiliaries for example by grinding and/or screening a solid active ingredient, or active ingredient mixture, for example to obtain a specific particle size, and in the presence of at least one auxiliary for example by intimately mixing and/or grinding the active ingredient, or active ingredient mixture, with the auxiliary (or auxiliaries). These processes for the preparation of the compositions according to the invention and the use of the compounds of the formula (I) for the preparation of these compositions are also subjects of the invention.

The methods of application for the compositions, i.e. the methods of controlling pests of the abovementioned type, such as spraying, atomizing, dusting, brushing on, seed-dressing, scattering or pouring, which are to be selected to suit the intended aims and the prevailing circumstances, and the use of the compositions for controlling pests of the abovementioned type are also subjects of the invention. Typical use concentrations are between 0.1 and 1000 ppm, preferably between 0.1 and 500 ppm, of active ingredient. The rates of application per hectare are generally 1 to 2000 g of active ingredient per hectare, in particular 10 to 1000 g/ha, preferably 20 to 600 g/ha.

A preferred method of application in the field of crop protection is application to the foliage of the plant (foliar application), it being possible to adjust frequency and rate of application to the degree or risk of infestation with the pest in question. Alternatively, the active ingredient can reach the plants via the root system (systemic action), by drenching the locus of the plants with a liquid composition or by incorporating the active ingredient in solid form into the locus of the plants, for example in the soil, for example in the form of granules (soil application). In the case of paddy rice crops, such granules can be metered into the flooded paddy field.

The compositions according to the invention are also suitable for the protection of plant propagation material, e.g. seed such as fruits, tubers or kernels, or nursery plants, against fungal infection and animal pests. The propagation material can be dressed with the composition before planting, for example seed can be dressed before sowing. It is also possible to apply the active ingredients according to the invention to seed kernels (coating), either by soaking the kernels in a liquid composition or by coating them with a solid composition. Alternatively, the composition can be applied to the site of application when the propagation material is planted, for example into the seed furrow during sowing. These treatment methods for plant propagation material and the plant propagation material treated accordingly are further subjects of the invention.

The examples which follow are intended to illustrate the invention. They do not limit the invention. Temperatures are given in degrees Celsius.

PREPARATION EXAMPLES

Example H1

N'-(2,6-dichloro-4-trifluoromethylphenyl)-4-cyanobenzohydrazide

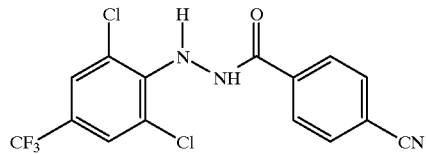

A solution of 14.2 g of 4-cyanobenzoyl chloride in 100 ml of methylene chloride is added dropwise with stirring at from 10 to 15° in the course of approximately 30 minutes to 20 g of 2,6-dichloro-4-trifluoromethylphenylhydrazine in 250 ml of dichloromethane, and the mixture is stirred for a further 16 hours. 36 ml of aqueous sodium hydroxide solution (10%) is then run in with vigorous stirring. 100 ml of methylene chloride are added, the organic phase is washed three times using in each case 100 ml of water and dried over sodium sulfate, and the solvent is removed on a rotary evaporator. After the residue has been recrystallized from toluene, the title product of melting point 185–186° is obtained (compound no. 1.6).

Example H2

The other compounds listed in Table 1 can also be prepared analogously to the procedure described in Example H1.

TABLE 1

![Structure: (R3a)n1-phenyl-N(R2)-NH-C(=O)-phenyl-(R3b)n2]

| No. | $(R_{3a})_{n1}$ | $(R_{3b})_{n2}$ | $R_2$ | Melting point (° C.) |
|---|---|---|---|---|
| 1.1 | 2-Cl, 4-CF$_3$ | 4-Cl | H | 167–170 |
| 1.2 | 2-Cl, 4-CF$_3$ | 4-NO$_2$ | H | 208–209 |
| 1.3 | 2-Cl, 4-CF$_3$ | 2-Cl | H | 170–171 |
| 1.4 | 2,6-Cl$_2$, 4-CF$_3$ | 4-CF$_3$ | H | 192–193 |
| 1.5 | 2,4-Cl$_2$ | 4-CF$_3$ | H | 189–190 |
| 1.6 | 2,6-Cl$_2$, 4-CF$_3$ | 4-CN | H | 185–186 |
| 1.7 | 4-CF$_3$ | 4-CN | H | 201–203 |
| 1.8 | 4-CF$_3$ | 4-CF$_3$ | H | 202–203 |
| 1.9 | 2,6-Cl$_2$, 4-CF$_3$ | 3-CN | H | 188–189 |
| 1.10 | 2,6-Cl$_2$ 4-CF$_3$ | 3-CF$_3$ | H | 137–138 |
| 1.11 | 3,5-CF$_3$ | 4-CN | H | 214–215 |
| 1.12 | 2-Cl, 4-CF$_3$ | 4-CN | H | 215–216 |
| 1.13 | 2,6-Cl$_2$, 4-CF$_3$ | 4-NO$_2$ | H | 192–193 |
| 1.14 | 2,4,6-Cl$_3$ | 4-CN | H | 189–190 |
| 1.15 | 2,6-Cl$_2$-4-CF$_3$ | 2-Cl-4-NO$_2$ | H | 205–206 |
| 1.16 | 2,6-Cl$_2$-4-CF$_3$ | 2,4-(NO$_2$)$_2$ | H | 218–219 |
| 1.17 | 2,6-Cl$_2$-4-CF$_3$ | 3-OCH$_3$-4-NO$_2$ | H | 194–195 |
| 1.18 | 2,6-Cl$_2$-4-CF$_3$ | 3-CH$_3$-4-NO$_2$ | H | 192–193 |
| 1.19 | 2,4,6-Cl$_3$ | 4-NO$_2$ | H | 201–202 |
| 1.20 | 2,6-Cl$_2$-4-NO$_2$ | 4-NO$_2$ | H | 242–243 |
| 1.21 | 2,6-Cl$_2$-4-NO$_2$ | 4-CN | H | 217–218 |
| 1.22 | 2,6-(CH$_3$)$_2$-4-Br | 4-CN | H | 181–182 |
| 1.23 | 2-Cl-4-Br-6-CH$_3$ | 4-CN | H | 185–186 |
| 1.24 | 2-Cl-4-Br-6-CH$_3$ | 4-NO$_2$ | H | 200–201 |
| 1.25 | 2,6-(CH$_3$)$_2$-4-Br | 4-NO$_2$ | H | 206–207 |
| 1.26 | 2,4,6-Cl$_3$ | 3-NO$_2$-4-Cl | H | 201–202 |
| 1.27 | 2,4,6-Cl$_3$ | 4-CHO | H | 175–176 |
| 1.28 | 2,6-Cl$_2$-4-CF$_3$ | 4-Br | H | 207–208 |
| 1.29 | 2,4-Cl$_2$-6-CF$_3$ | 4-NO$_2$ | H | 184–185 |
| 1.30 | 2,6-Cl$_2$-3-F-4-CF$_3$ | 4-NO$_2$ | H | 208–209 |
| 1.31 | 2,6-Cl$_2$-4-CF$_3$ | 4-COCF$_3$ | H | 182–183 |
| 1.32 | 2,6-Cl$_2$-4-CF$_3$ | 4-CO$_2$CH$_3$ | H | 213–214 |
| 1.33 | 2-Cl-4-CF$_3$-6-F | 4-NO$_2$ | H | 168–170 |
| 1.34 | 2,3,6-Cl$_3$-4-CF$_3$ | 4-NO$_2$ | H | 210–212 |

TABLE 2

![Structure: (R3a)n1-phenyl-N(R2)-N=C(Cl)-phenyl-(R3b)n2]

| No. | $(R_{3a})_{n1}$ | $(R_{3b})_{n2}$ | $R_2$ | Melting point (° C.) |
|---|---|---|---|---|
| 2.1 | 2-Cl, 4-CF$_3$ | 4-Cl | H | 116–117 |
| 2.2 | 2-Cl, 4-CF$_3$ | 4-NO$_2$ | H | 181–183 |
| 2.3 | 2,6-Cl$_2$, 4-CF$_3$ | 4-CF$_3$ | H | 136–137 |
| 2.4 | 2,4-Cl$_2$ | 4-CF$_3$ | H | 127–128 |
| 2.5 | 2,6-Cl$_2$, 4-CF$_3$ | 4-CN | H | 168–169 |
| 2.6 | 4-CF$_3$ | 4-CN | H | 174–176 |
| 2.7 | 4-CF$_3$ | 4-CF$_3$ | H | 127–128 |
| 2.8 | 2,6-Cl$_2$, 4-CF$_3$ | 3-CN | H | 157–158 |
| 2.9 | 2,6-Cl$_2$, 4-CF$_3$ | 3-CF$_3$ | H | 97–98 |
| 2.10 | 3,5-(CF$_3$)$_2$ | 4-CN | H | 234–236 |
| 2.11 | 2-Cl, 4-CF$_3$ | 4-CN | H | 170–171 |
| 2.12 | 2,6-Cl$_2$, 4-CF$_3$ | 4-NO$_2$ | H | 119–120 |
| 2.13 | 2,4,6-Cl$_3$ | 4-CN | H | 184–185 |
| 2.14 | 2,6-Cl$_2$, 4-CF$_3$ | 4-Cl | H | 170–171 |
| 2.15 | 2,6-Cl$_2$, 4-CF$_3$ | 3-CH$_3$, 4-NO$_2$ | H | 154–155 |
| 2.16 | 2,6-Cl$_2$, 4-CF$_3$ | 3-OCH$_3$, 4-NO$_2$ | H | 169–170 |
| 2.17 | 2,4,6-Cl$_3$ | 4-NO$_2$ | H | 162–163 |
| 2.18 | 2,6-Cl$_2$, 4-NO$_2$ | 4-CN | H | 233–234 |
| 2.19 | 2,6-(CH$_3$)$_2$, 4-Br | 4-CN | H | 144–146 |
| 2.20 | 2,6-(CH$_3$)$_2$, 4-Br | 4-NO$_2$ | H | 143–144 |
| 2.21 | 2-Cl-4-Br-6-CH$_3$ | 4-CN | H | 172–173 |
| 2.22 | 2-Cl-4-Br-6-CH$_3$ | 4-NO$_2$ | H | 156–157 |
| 2.23 | 2,4,6-Cl$_3$ | 3-NO$_2$, 4-Cl | H | 182–183 |
| 2.24 | 2,6-Cl$_2$, 4-NO$_2$ | 4-NO$_2$ | H | 199–200 |
| 2.25 | 2,4,6-Cl$_3$ | 4-CHO | H | 135–137 |
| 2.26 | 2,6-Cl$_2$, 4-CF$_3$ | 4-Br | H | 124–125 |
| 2.27 | 2,4-Cl$_2$, 6-CF$_3$ | 4-NO$_2$ | H | 128–129 |
| 2.28 | 2,6-Cl$_2$-3-F-4-CF$_3$ | 4-NO$_2$ | H | 143–144 |
| 2.29 | 2,6-Cl$_2$, 4-CF$_3$ | 4-C(O)CF$_3$ | H | 107–108 |
| 2.30 | 2-Cl-4-CF$_3$-6-F | 4-NO$_2$ | H | 135–137 |
| 2.31 | 2,3,6-Cl$_3$-4-CF$_3$ | 4-NO$_2$ | H | 121–123 |

Example H3

4-{1-[(2,6-dichloro-4-trifluoromethylphenyl)hydrazono]-chloromethyl}benzonitrile

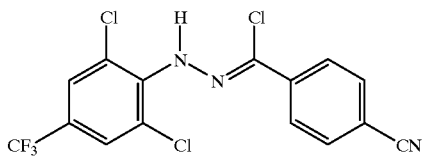

12.6 g of thionyl chloride are added dropwise with stirring to a solution of 26.6 g of N'-(2,6-dichloro-4-trifluoromethyl)phenyl-4-cyanobenzohydrazide in 250 ml of toluene at room temperature. The mixture is then heated to 90° and stirred for 5 hours. The mixture is evaporated to dryness on a rotary evaporator and the residue is crystallized from hexane/toluene 1:1. This gives the title compound of melting point 168–169° (compound no. 2.5).

Example H4

The other compounds listed in Table 2 can also be prepared analogously to the procedure described in Example H3.

Example H5

4-{1-[(2,6-dichloro-4-trifluoromethylphenyl)hydrazono]-2-nitriloethyl}benzonitrile 55 g of solid 4-{1-[(2,6-dichloro-4-trifluoromethylphenyl)hydrazono]chloromethyl}benzonitrile are added in portions in the course of approximately one hour to 11.4 g of sodium cyanide in 270 ml of water and 400 ml of ethanol. After the mixture has been stirred for three hours at room temperature, 200 ml of ethanol and 135 ml of water are added and the mixture is stirred for a further 5 hours. 100 ml of water are added slowly, the precipitate is filtered off and washed with water, and the filter residue is dried in vacuo at 40°. This gives the title compound of melting point 186–187° (compound no. 3.4).

Example H6

4-{1-[(2,6-dichloro-4-trifluoromethylphenyl)hydrazono]-2-nitriloethyl}chlorobenzene

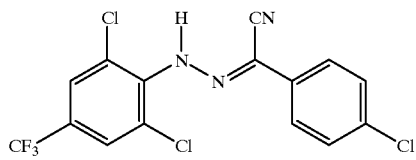

a) 1.5 g of sodium nitrite are added at room temperature to a mixture of 14 ml of concentrated sulfuric acid and 14 ml of acetic acid. The mixture is heated to 80° and stirred until all solids have dissolved, and the solution is cooled to room temperature. To this mixture there are added 4.6 g of 2,6-dichloro-4-trifluoromethylaniline, dissolved in 14 ml of concentrated sulfuric acid, and the mixture is stirred for one hour at room temperature and then for one hour at 50°.

b) The solution prepared in accordance with a) is added with stirring at room temperature to 3.85 g of 3-oxo-2-(4-chlorophenyl)butyronitrile in 28 ml of acetic acid and 40 ml of water, and the mixture is stirred for a further three hours. The mixture is poured into 300 ml of ice-water and extracted three times using in each case 100 ml of ethyl acetate. The combined organic phases are washed with water, dried over sodium sulfate and evaporated to dryness in vacuo. The residue is crystallized from toluene/hexane 1:1. This gives the title compound of melting point 164–165° (compound no. 3.16).

Example H7

4-{1-[(2,6-dichloro-4-trifluoromethylphenyl)methylhydrazono]-2-nitriloethyl}benzonitrile

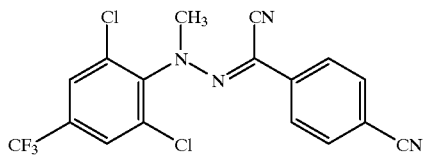

To 0.96 g of 4-{1-[(2,6-dichloro-4-trifluoromethylphenyl)hydrazono]-2-nitriloethyl}benzonitrile in 30 ml of ethyl methyl ketone there are added 0.7 g of finely pulverized potassium carbonate and 1.4 g of methyl iodide. The mixture is heated to 80° and stirred for three hours. The reaction mixture is filtered, the filtrate is concentrated in vacuo, and the residue is dissolved in ethyl acetate. The ethyl acetate phase is washed with water and NaCl solution, dried over sodium sulfate and evaporated to dryness in vacuo. After the residue has been washed with hexane, the title product of melting point 92–93° is obtained (compound no. 3.29).

Example H8 methyl{N'-[1-(4-cyanophenyl)-2-nitriloethylidene]-N-(2,6-dichloro-4-trifluoromethylphenyl)hydrazino]oxoacetate

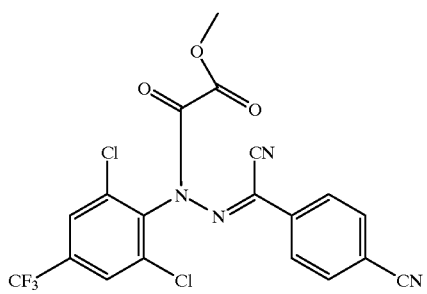

0.73 g of potassium tert-butoxide is added to 1.9 g of 4-{1-[(2,6-dichloro-4-trifluoromethylphenyl)hydrazono]nitrilomethyl}benzonitrile in 40 ml of anhydrous tetrahydrofuran. A solution of 0.8 g of methyl chlorooxalate in 5 ml of tetrahydrofuran is added dropwise at 10° and the mixture stirred for 2 hours. The reaction mixture is evaporated to dryness, the residue is taken up in ethyl acetate, and the organic phase is washed with water and dried over sodium sulfate. The solvent is evaporated and the residue is chromatographed on silica gel using n-hexane/diethyl ether (3:1) as the eluent. This gives the title product of melting point 194–195° (compound no. 3.36).

Example H9

The other compounds listed in Tables 3 and 4 can also be prepared analogously to the procedure described for Examples H5 to H8.

TABLE 3

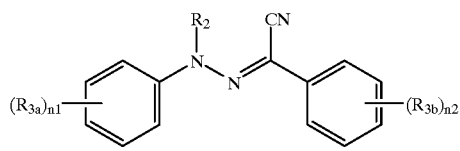

| No. | $(R_{3a})_{n1}$ | $(R_{3b})_{n2}$ | $R_2$ | Melting point (° C.) |
|-----|-----------------|-----------------|-------|----------------------|
| 3.1 | 2-Cl, 4-CF$_3$ | 4-Cl | H | 161–162 |
| 3.2 | 2-Cl, 4-CF$_3$ | 4-NO$_2$ | H | 204–205 |
| 3.3 | 2,6-Cl$_2$, 4-CF$_3$ | 4-CF$_3$ | H | 133–136 |
| 3.4 | 2,6-Cl$_2$, 4-CF$_3$ | 4-CN | H | 186–187 |
| 3.5 | 2,4-Cl$_2$ | 4-CF$_3$ | H | 160–161 |
| 3.6 | 2,6-Cl$_2$, 4-CF$_3$ | 3-CN | H | 180–181 |
| 3.7 | 2,6-Cl$_2$, 4-CF$_3$ | 3-CF$_3$ | H | 119–121 |
| 3.8 | 3,5-(CF$_3$)$_2$ | 2-F | H | 198–199 |
| 3.9 | 3,5-(CF$_3$)$_2$ | 4-CN | H | 272 (decomp.) |
| 3.10 | 2-NO$_2$ | 4-NO$_2$ | H | 211–213 |

TABLE 3-continued

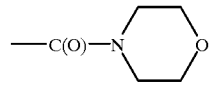

| No. | $(R_{3a})_{n1}$ | $(R_{3b})_{n2}$ | $R_2$ | Melting point (° C.) |
|---|---|---|---|---|
| 3.11 | 4-CN | 4-Cl | H | 240–242 |
| 3.12 | 2-CN | 4-Cl | H | 168–170 |
| 3.13 | 3-CN | 4-Cl | H | 189–191 |
| 3.14 | 4-O—$CF_3$ | 4-Cl | H | 162–163 |
| 3.15 | 4-$CF_3$ | 4-Cl | H | 193–194 |
| 3.16 | 2,6-$Cl_2$, 4-$CF_3$ | 4-Cl | H | 164–165 |
| 3.17 | 2,6-$Cl_2$, 4-$CF_3$ | 4-O—$CF_3$ | H | 133–134 |
| 3.18 | 2,6-$Cl_2$, 4-$CF_3$ | 3,5-$(CF_3)_2$ | H | 121–122 |
| 3.19 | 2-Cl, 4-$CF_3$ | 4-O—$CF_3$ | H | 104–106 |
| 3.20 | 2-Cl, 4-$CF_3$ | 3,5-$(CF_3)_2$ | H | 129–131 |
| 3.21 | 2,6-$Cl_2$, 4-$CF_3$ | 3,5-$F_2$ | H | 148–150 |
| 3.22 | 2-Cl, 4-$CF_3$ | 3,5-$F_2$ | H | 158–159 |
| 3.23 | 2-Cl, 4-$CF_3$ | 3-$CF_3$ | H | 110–112 |
| 3.24 | 4-$CF_3$ | 4-$CF_3$ | H | 185–186 |
| 3.25 | 2-Cl, 4-$CF_3$ | 4-CN | H | 189–190 |
| 3.26 | 2,6-$Cl_2$, 4-$CF_3$ | 3,4-$Cl_2$ | H | 163–164 |
| 3.27 | 2,6-$Cl_2$, 4-$CF_3$ | 3,4-$Cl_2$ | —$CH_3$ | |
| 3.28 | 2,6-$Cl_2$, 4-$CF_3$ | 3,4-$Cl_2$ | —$COCOOC_2H_5$ | |
| 3.29 | 2,6-$Cl_2$, 4-$CF_3$ | 4-CN | —$CH_3$ | 92–93 |
| 3.30 | 2,6-$Cl_2$, 4-$CF_3$ | 4-CN | —$CH_2OC_2H_5$ | Resin |
| 3.31 | 2,6-$Cl_2$, 4-$CF_3$ | 4-CN | —$CH_2C_6H_5$ | Resin |
| 3.32 | 2,6-$Cl_2$, 4-$CF_3$ | 4-CN | —$COCH_3$ | 191–192 |
| 3.33 | 2,6-$Cl_2$, 4-$CF_3$ | 4-CN | —$CH_2C_6H_4$-2-$NO_2$ | 109–111 |
| 3.34 | 2,6-$Cl_2$, 4-$CF_3$ | 4-CN | —$COOC_2H_5$ | 141–142 |
| 3.35 | 2,6-$Cl_2$, 4-$CF_3$ | 4-CN | CN | 117–118 |
| 3.36 | 2,6-$Cl_2$, 4-$CF_3$ | 4-CN | —$COCOOCH_3$ | 194–195 |
| 3.37 | 2-Cl, 4-$CF_3$ | 4-CN | —$CH_2OC_2H_5$ | Resin |
| 3.38 | 2-Cl, 4-$CF_3$ | 4-CN | —$CH_2C_6H_5$ | Resin |
| 3.39 | 2-Cl, 4-$CF_3$ | 4-CN | —$CH_2C_6H_4$-2-$NO_2$ | 81–83 |
| 3.40 | 2-Cl, 4-$CF_3$ | 4-CN | $CH_3$ | 153–154 |
| 3.41 | 2-Cl, 4-$CF_3$ | 4-CN | —$COCH_3$ | 124–125 |
| 3.42 | 2-Cl, 4-$CF_3$ | 4-CN | 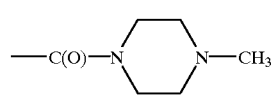 | "Foam" |
| 3.43 | 2,4,6-$Cl_3$ | 4-CN | H | 170–171 |
| 3.44 | 2,6-$Cl_2$, 4-$CF_3$ | 2,6-$F_2$ | H | 108–109 |
| 3.45 | 2,6-$Cl_2$, 4-$CF_3$ | 4-CN | —$CONHC_2H_5$ | 211–212 |
| 3.46 | 2,6-$Cl_2$, 4-$CF_3$ | 4-CN | —$CONHC_6H_4$-4-$OCF_3$ | 217–218 |
| 3.47 | 2,6-$Cl_2$, 4-$CF_3$ | 4-CN | —C(O)—N⟨piperazine⟩N—$CH_3$ | Resin |
| 3.48 | 2,6-$Cl_2$, 4-$CF_3$ | 4-CN | —CO-cyclo-$C_3H_5$ | 192–193 |
| 3.49 | 2,6-$Cl_2$, 4-$CF_3$ | 4-CN | —$COC_6H_4$-4-Cl | 168–170 |
| 3.50 | 2,6-$Cl_2$, 4-$CF_3$ | 4-$NO_2$ | H | 162–163 |
| 3.51 | 2,6-$Cl_2$, 4-$CF_3$ | 4-CN | —$C_2H_5$ | Resin |
| 3.52 | 2,6-$Cl_2$, 4-$CF_3$ | 4-CN | n-$C_3H_7$ | 95–96 |
| 3.53 | 2,6-$Cl_2$, 4-$CF_3$ | 4-CN | i-$C_3H_7$ | |
| 3.54 | 2,6-$Cl_2$, 4-$CF_3$ | 4-CN | —$CO(CH_2)_3CH$=$CF_2$ | 120–121 |
| 3.55 | 2,6-$Cl_2$, 4-$CF_3$ | 3,5-$Cl_2$ | H | |
| 3.56 | 2,6-$Cl_2$, 4-$CF_3$ | 3,5-$Cl_2$ | —$CH_3$ | |
| 3.57 | 2,6-$Cl_2$, 4-$CF_3$ | 3,5-$Cl_2$ | —$COOC_2H_5$ | |
| 3.58 | 2,6-$Cl_2$, 4-$CF_3$ | 2,3-$Cl_2$ | H | |
| 3.59 | 2,6-$Cl_2$, 4-$CF_3$ | 2,3-$Cl_2$ | —$CH_3$ | |
| 3.60 | 2,6-$Cl_2$, 4-$CF_3$ | 2,3-$Cl_2$ | —$CH_2OC_2H_5$ | |
| 3.61 | 2,6-$Cl_2$, 4-$CF_3$ | 2,5-$Cl_2$ | H | |
| 3.62 | 2,6-$Cl_2$, 4-$CF_3$ | 2,5-$Cl_2$ | —$CH_3$ | |
| 3.63 | 2,6-$Cl_2$, 4-$CF_3$ | 2,5-$Cl_2$ | —$C_2H_5$ | |
| 3.64 | 2-Cl, 4-$CF_3$ | 3,4-$Cl_2$ | H | |
| 3.65 | 2-Cl, 4-$CF_3$ | 3,5-$Cl_2$ | H | |
| 3.66 | 2-Cl, 4-$CF_3$ | 3,5-$Cl_2$ | —$CH_3$ | |
| 3.67 | 3-$CF_3$ | 4-CN | H | |

TABLE 3-continued

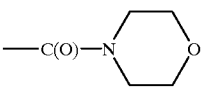

| No. | $(R_{3a})_{n1}$ | $(R_{3b})_{n2}$ | $R_2$ | Melting point (° C.) |
|---|---|---|---|---|
| 3.68 | 3-$CF_3$ | 4-CN | —$CH_3$ | |
| 3.69 | 2-Cl | 4-CN | H | |
| 3.70 | 2,3-$Cl_2$ | 4-CN | H | |
| 3.71 | 2,3-$Cl_2$ | 4-CN | —$CH_3$ | |
| 3.72 | 2,4-$Cl_2$ | 4-CN | H | |
| 3.73 | 2,4-$Cl_2$ | 4-CN | —$CH_3$ | |
| 3.74 | 2,4-$Cl_2$ | 4-CN | —$COOCH_3$ | |
| 3.75 | 2,6-$Cl_2$, 4-$CF_3$ | 4-CN | —C(O)—N(morpholine) | amorphous |
| 3.76 | 2,6-$Cl_2$, 4-$CF_3$ | 4-CN | —$CH_2CN$ | 201–202 |
| 3.77 | 2,6-$Cl_2$, 4-$CF_3$ | 4-$NO_2$ | —$CH_3$ | 135–137 |
| 3.78 | 2,6-$Cl_2$, 4-$CF_3$ | 4-CN | —$CH_2CCH$ | 116–117 |
| 3.79 | 2,6-$Cl_2$, 4-$CF_3$ | 4-CN | —$CH_2N(CH_3)CO_2CH_3$ | 96–98 |
| 3.80 | 2,6-$Cl_2$, 4-$CF_3$ | 4-CN | —$CH_2N(CH_3)CO_2C_2H_5$ | 78–80 |
| 3.81 | 2,6-$Cl_2$, 4-$CF_3$ | 2-CN, 4-$CF_3$ | H | 124–125 |
| 3.82 | 2,6-$Cl_2$, 4-$CF_3$ | 2-F, 4-CN | H | 192–193 |
| 3.83 | 2,6-$Cl_2$, 4-$CF_3$ | 3-Cl, 4-CN | H | 179–180 |
| 3.84 | 2,6-$Cl_2$, 4-$CF_3$ | 4-CN | —$CO_2CH_3$ | 122–123 |
| 3.85 | 2,6-$Cl_2$, 4-$CF_3$ | 4-CN | —$CO_2CH_2CH_2Cl$ | 125–126 |
| 3.86 | 2,6-$Cl_2$, 4-$CF_3$ | 4-CN | —$CO_2C_6H_5$ | 105–107 |
| 3.87 | 2,6-$Cl_2$, 4-$CF_3$ | 4-CN | —$CO_2CH_2C_6H_5$ | 158–159 |
| 3.88 | 2,6-$Cl_2$, 4-$CF_3$ | 4-CN | —$CO_2CH_2CH(CH_3)_2$ | 157–158 |
| 3.89 | 2,6-$Cl_2$, 4-$CF_3$ | 4-CN | —$CO_2C_8H_{17}$ | 61–62 |
| 3.90 | 2,6-$Cl_2$, 4-$CF_3$ | 4-$NO_2$ | —$CO_2C_2H_5$ | 133–134 |
| 3.91 | 2,6-$Cl_2$, 4-$CF_3$ | 4-$NO_2$ | —$CH_2OC_2H_5$ | 73–74 |
| 3.92 | 2,6-$Cl_2$, 4-$CF_3$ | 4-$NO_2$ | —$C_2H_5$ | 96–97 |
| 3.93 | 2,6-$Cl_2$, 4-$CF_3$ | 3-$OCH_3$, 4-$NO_2$ | H | 146–147 |
| 3.94 | 2,6-$Cl_2$, 4-$CF_3$ | 3-$CH_3$, 4-$NO_2$ | H | 172–173 |
| 3.95 | 2,6-$Cl_2$, 4-$CF_3$ | 2-Cl, 4-$NO_2$ | H | 164–165 |
| 3.96 | 2,4,6-$Cl_3$ | 4-$NO_2$ | H | 180–181 |
| 3.97 | 2,6-$Cl_2$, 4-$CF_3$ | 4-$NO_2$ | —$CH_2N(CH_3)CO_2C_2H_5$ | 100–101 |
| 3.98 | 2,6-$Cl_2$, 4-$CF_3$ | 4-$NO_2$ | —$COCH_3$ | 175–176 |
| 3.99 | 2,6-$Cl_2$, 4-$CF_3$ | 4-$NO_2$ | —$CH_2CCH$ | 165–166 |
| 3.100 | 2,6-$Cl_2$, 4-$CF_3$ | 4-$NO_2$ | —$CH_2C_6H_4$-4-$NO_2$ | 133–135 |
| 3.101 | 2,6-$Cl_2$, 4-$CF_3$ | 4-CN | —$COCONHC_2H_5$ | 155–157 |
| 3.102 | 2,6-$Cl_2$, 4-$CF_3$ | 2-$NO_2$, 4-$CF_3$ | H | 116–117 |
| 3.103 | 2,6-$Cl_2$, 4-$CF_3$ | 2,4-$(NO_2)_2$ | H | 143–145 |
| 3.104 | 2,6-$Cl_2$, 4-$CF_3$ | 2-$NO_2$ | H | 134–135 |
| 3.105 | 2,6-$Cl_2$, 4-$NO_2$ | 2-$NO_2$, 4-$CF_3$ | H | 100–102 |
| 3.106 | 2,6-$Cl_2$, 4-$NO_2$ | 4-$NO_2$ | H | 195–196 |
| 3.107 | 2,6-$Cl_2$, 4-$NO_2$ | 4-CN | H | 226–227 |
| 3.108 | 2-Cl, 4-Br, 6-$CH_3$ | 4-$NO_2$ | H | 185–186 |
| 3.109 | 2-Cl, 4-Br, 6-$CH_3$ | 4-CN | H | 181–182 |
| 3.110 | 2,6-$(CH_3)_2$, 4-Br | 4-CN | H | 194–195 |
| 3.111 | 2,6-$(CH_3)_2$, 4-Br | 4-$NO_2$ | H | 197–198 |
| 3.112 | 2,4,6-$Cl_3$ | 4-$NO_2$ | —$CH_2N(CH_3)CO_2C_2H_5$ | 110–112 |
| 3.113 | 2,4,6-$Cl_3$ | 4-$NO_2$ | —$CH_2OC_2H_5$ | 139–141 |
| 3.114 | 2,4,6-$Cl_3$ | 4-$NO_2$ | —$CO_2C_2H_5$ | 108–110 |
| 3.115 | 2,4,6-$Cl_3$ | 4-$NO_2$ | —$C_2H_5$ | 94–96 |
| 3.116 | 2,6-$Cl_2$, 4-$CF_3$ | 2-Cl, 4-$NO_2$ | —$CH_2OC_2H_5$ | 78–79 |
| 3.117 | 2,6-$Cl_2$, 4-$CF_3$ | 2-Cl, 4-$NO_2$ | —$CO_2C_2H_5$ | 114–115 |
| 3.118 | 2,6-$Cl_2$, 4-$CF_3$ | 2-Cl, 4-$NO_2$ | —$CH_3$ | 144–145 |
| 3.119 | 2,4,6-$Cl_3$ | 4-Cl, 3-$NO_2$ | H | 168–169 |
| 3.120 | 2-Cl, 4-Br, 6-$CH_3$ | 4-CN | $CH_3$ | 140–142 |
| 3.121 | 2-Cl, 4-Br, 6-$CH_3$ | 4-CN | $C_2H_5$ | 94–95 |
| 3.122 | 2-Cl, 4-Br, 6-$CH_3$ | 4-CN | $CH_2OC_2H_5$ | 89–90 |
| 3.123 | 2-Cl, 4-Br, 6-$CH_3$ | 4-$NO_2$ | $CH_2OC_2H_5$ | 103–104 |
| 3.124 | 2-Cl, 4-Br, 6-$CH_3$ | 4-$NO_2$ | $CH_3$ | 163–164 |
| 3.125 | 2-Cl, 4-Br, 6-$CH_3$ | 4-$NO_2$ | $C_2H_5$ | 133–135 |
| 3.126 | 2,6-$(CH_3)_2$, 4-Br | 4-$NO_2$ | $CH_2OC_2H_5$ | 116–118 |
| 3.127 | 2,6-$(CH_3)_2$, 4-Br | 4-CN | $CH_2OC_2H_5$ | 82–83 |
| 3.128 | 2,6-$(CH_3)_2$, 4-Br | 4-$NO_2$ | $CH_3$ | 182–183 |
| 3.129 | 2,6-$(CH_3)_2$, 4-Br | 4-$NO_2$ | $C_2H_5$ | 160–161 |
| 3.130 | 2,6-$(CH_3)_2$, 4-Br | 4-CN | $CH_3$ | 145–146 |

TABLE 3-continued

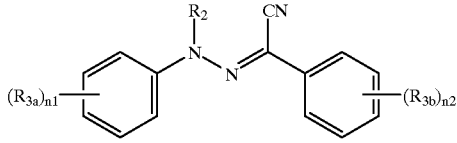

| No. | $(R_{3a})_{n1}$ | $(R_{3b})_{n2}$ | $R_2$ | Melting point (° C.) |
|---|---|---|---|---|
| 3.131 | 2,6-$(CH_3)_2$, 4-Br | 4-CN | $C_2H_5$ | 105–106 |
| 3.132 | 2,6-$Cl_2$, 4-$CF_3$ | 4-CN | $CH_2N(CH_3)SO_2CH_3$ | 143–145 |
| 3.133 | 2,6-$Cl_2$, 4-$CF_3$ | 4-$NO_2$ | $CH_2N(CH_3)SO_2CH_3$ | 156–158 |
| 3.134 | 2,6-$Cl_2$, 4-$CF_3$ | 4-$NO_2$ | $CH_2OCH_3$ | 109–110 |
| 3.135 | 2,6-$Cl_2$, 4-$CF_3$ | 4-CN | $CH_2N(CH_3)SO_2C_2H_5$ | 140–142 |
| 3.136 | 2,6-$Cl_2$, 4-$CF_3$ | 4-$NO_2$ | $CH_2N(CH_3)SO_2C_2H_5$ | 128–130 |
| 3.137 | 2,4,6-$Cl_3$ | 4-CHO | H | 152–154 |
| 3.138 | 2,6-$Cl_2$, 4-$CF_3$ | 4-CN | $CH_2N(CH_3)SO_2C_6H_5$ | 178–180 |
| 3.139 | 2,6-$Cl_2$, 4-$CF_3$ | 4-$NO_2$ | $CH_2N(CH_3)SO_2C_6H_5$ | 122–123 |
| 3.140 | 2,6-$Cl_2$, 4-$CF_3$ | 4-Br | H | 179–180 |
| 3.141 | 2,6-$Cl_2$, 4-$CF_3$ | 4-$NO_2$ | $COCO_2C_2H_5$ | 145–146 |
| 3.142 | 2,6-$Cl_2$, 4-$CF_3$ | 4-$NO_2$ | $COCONHC_2H_5$ | 145–147 |
| 3.143 | 2,6-$Cl_2$, 4-$NO_2$ | 4-$NO_2$ | $n$-$C_3H_7$ | 103–104 |
| 3.144 | 2,6-$Cl_2$, 4-$CF_3$ | 4-$NO_2$ | $COC_2H_5$ | 153–154 |
| 3.145 | 2,6-$Cl_2$, 4-$CF_3$ | 4-$NO_2$ | $CO_2CH_3$ | 129–130 |
| 3.146 | 2,6-$Cl_2$, 4-$CF_3$ | 4-$NO_2$ | $CO_2$—$CH_2CH_2$—Cl | 130–131 |
| 3.147 | 2,6-$Cl_2$, 4-$CF_3$ | 4-$COCF_3$ | H | 111–112 |
| 3.148 | 2,6-$Cl_2$, 4-$CF_3$ | 4-Br | $CH_2OC_2H_5$ | 78–79 |
| 3.149 | 2,6-$Cl_2$, 4-$CF_3$ | 4-$C_6H_4$-4-$CF_3$ | $CH_2OC_2H_5$ | 107–108 |
| 3.150 | 2,4,6-$Cl_3$ | 4-Cl, 3-$NO_2$ | $CH_3$ | |
| 3.151 | 2,4,6-$Cl_3$ | 4-Cl, 3-$NO_2$ | $C_2H_5$ | |
| 3.152 | 2,4,6-$Cl_3$ | 4-Cl, 3-$NO_2$ | $CH_2OC_2H_5$ | |
| 3.153 | 2,4,6-$Cl_3$ | 4-Cl, 3-$NO_2$ | $CO_2C_2H_5$ | |
| 3.154 | 2,6-$Cl_2$, 4-$CF_3$ | 4-Cl, 3-$NO_2$ | H | |
| 3.155 | 2,6-$Cl_2$, 4-$CF_3$ | 4-Cl, 3-$NO_2$ | $CH_3$ | |
| 3.156 | 2,6-$Cl_2$, 4-$CF_3$ | 4-Cl, 3-$NO_2$ | $C_2H_5$ | |
| 3.157 | 2,6-$Cl_2$, 4-$CF_3$ | 4-Cl, 3-$NO_2$ | $CH_2OC_2H_5$ | |
| 3.158 | 2,6-$Cl_2$, 4-$CF_3$ | 4-Cl, 3-$NO_2$ | $CO_2C_2H_5$ | |
| 3.159 | 2,6-$Cl_2$, 4-$CF_3$ | 4-$NO_2$ | $i$-$C_3H_7$ | 124–126 |
| 3.160 | 2,6-$Cl_2$, 4-$CF_3$ | 4-$NO_2$ | —$CH_2SCH_3$ | 112–113 |
| 3.161 | 2,6-$Cl_2$, 4-$CF_3$ | 4-$NO_2$ | —CN | 111–112 |
| 3.162 | 2,6-$Cl_2$, 4-$CF_3$ | 4-$NO_2$ | —$CH_2CH=CH_2$ | 60–61 |
| 3.163 | 2,6-$Cl_2$, 4-$CF_3$ | 4-$NO_2$ | —$CH_2CN$ | 187–188 |
| 3.164 | 2,4-$Cl_2$, 6-$CF_3$ | 4-$NO_2$ | H | 135–136 |
| 3.165 | 2,4-$Cl_2$, 6-$CF_3$ | 4-$NO_2$ | —$CH_2OC_2H_5$ | 111–113 |
| 3.166 | 2,6-$Cl_2$, 4-$CF_3$ | 4-$NO_2$ | —$C(O)(CH_2)_3CH=CF_2$ | 124–125 |
| 3.167 | 2,6-$Cl_2$, 3-F, 4-$CF_3$ | 4-$NO_2$ | H | 155–156 |
| 3.168 | 2,6-$Cl_2$, 4-$CF_3$ | 4-$NO_2$ | —$CH_2CH=CCl_2$ | 111–113 |
| 3.169 | 2,6-$Cl_2$, 4-$CF_3$ | 4-$NO_2$ | —$C(O)$-$c$-$C_3H_5$ | 199–200 |
| 3.170 | 2,6-$Cl_2$, 3-F, 4-$CF_3$ | 4-$NO_2$ | —$CH_2OC_2H_5$ | 89–90 |
| 3.171 | 2,6-$Cl_2$, 3-F, 4-$CF_3$ | 4-$NO_2$ | —$CO_2C_2H_5$ | 126–127 |
| 3.172 | 2,6-$Cl_2$, 3-F, 4-$CF_3$ | 4-$NO_2$ | —$CH_3$ | 164–165 |
| 3.173 | 2,6-$Cl_2$, 3-F, 4-$CF_3$ | 4-$NO_2$ | —$C_2H_5$ | 109–111 |
| 3.174 | 2,6-$Cl_2$, 4-$CF_3$ | 4-$C_6H_4$-(4-$CF_3$) | —$CH_2OC_2H_5$ | 107–108 |
| 3.175 | 2,6-$Cl_2$, 4-$CF_3$ | 4-$NO_2$ | —$CH_2SC_6H_5$ | 132–134 |
| 3.176 | 2,6-$Cl_2$, 4-$CF_3$ | 4-$C_6H_4$-(4-Cl) | —$CH_2OC_2H_5$ | 93–95 |
| 3.177 | 2-Cl, 4-$CF_3$, 6-F | 4-$NO_2$ | H | 169–170 |
| 3.178 | 2-Cl, 4-$CF_3$, 6-F | 4-$NO_2$ | —$CH_3$ | 74–76 |
| 3.179 | 2-Cl-4-$CF_3$-6-F | 4-$NO_2$ | —$C_2H_5$ | 111–112 |
| 3.180 | 2-Cl, 4-$CF_3$, 6-F | 4-$NO_2$ | —$CH_2OC_2H_5$ | Oil |
| 3.181 | 2-Cl, 4-$CF_3$, 6-F | 4-$NO_2$ | —$CO_2C_2H_5$ | 106–108 |
| 3.182 | 2,6-$Cl_2$, 4-$CF_3$ | 4-$C_6H_3$-(3,5-$(CF_3)_2$) | —$CH_2OC_2H_5$ | 80–81 |
| 3.183 | 2,6-$Cl_2$, 4-$CF_3$ | 4-$C_6H_4$-(4-F) | —$CH_2OC_2H_5$ | 81–82 |
| 3.184 | 2,6-$Cl_2$, 4-$CF_3$ | 4-$C_6H_3$-(2,4-$Cl_2$) | —$CH_2OC_2H_5$ | 55–57 |
| 3.185 | 2,6-$Cl_2$, 4-$CF_3$ | 4-$C_6H_3$-(3,5-$Cl_2$) | —$CH_2OC_2H_5$ | 91–93 |
| 3.186 | 2,6-$Cl_2$, 4-$CF_3$ | 4-$C_6H_4$-(3-$CF_3$) | —$CH_2OC_2H_5$ | 58–60 |
| 3.187 | 2,6-$Cl_2$, 4-$CF_3$ | 4-$C_6H_3$-(3-Cl-4-F) | —$CH_2OC_2H_5$ | 78–79 |
| 3.188 | 2,6-$Cl_2$, 4-$CF_3$ | 4-$C_6H_4$-(3-$NO_2$) | —$CH_2OC_2H_5$ | 104–105 |
| 3.189 | 2,3,6-$Cl_3$, 4-$CF_3$ | 4-$NO_2$ | H | 143–145 |
| 3.190 | 2,3,6-$Cl_3$, 4-$CF_3$ | 4-$NO_2$ | —$CH_3$ | 185–187 |
| 3.191 | 2,3,6-$Cl_3$, 4-$CF_3$ | 4-$NO_2$ | —$C_2H_5$ | 104–105 |
| 3.192 | 2,3,6-$Cl_3$, 4-$CF_3$ | 4-$NO_2$ | —$CH_2OC_2H_5$ | 88–90 |
| 3.193 | 2,3,6-$Cl_3$, 4-$CF_3$ | 4-$NO_2$ | —$CO_2C_2H_5$ | 152–153 |

TABLE 4

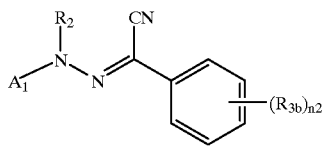

| No. | $A_1$ | $(R_{3b})_{n2}$ | $R_2$ | Melting point (° C.) |
|---|---|---|---|---|
| 4.1 | 2-pyridyl | 4-Cl | H | |
| 4.2 | 3-pyridyl | 4-Cl | H | |
| 4.3 | 4-pyridyl | 4-Cl | H | |
| 4.4 | 2-pyridyl | 4-CN | H | |
| 4.5 | 3-pyridyl | 4-CN | H | |
| 4.6 | 3-pyridyl | 4-CN | —$CH_3$ | |
| 4.7 | 3-pyridyl | 4-CN | —$COOC_2H_5$ | |
| 4.8 | 3-pyridyl | 4-CN | —$COOCH_3$ | |
| 4.9 | 3-pyridyl | 4-CN | —$CH_2OC_2H_5$ | |
| 4.10 | 4-pyridyl | 4-CN | H | |
| 4.11 | 2-pyridyl | 4-$CF_3$ | H | |
| 4.12 | 3-pyridyl | 4-$CF_3$ | H | |
| 4.13 | 4-pyridyl | 4-$CF_3$ | H | |
| 4.14 | 2-pyridyl | 4-$CF_3$ | —$COOCH_3$ | |
| 4.15 | 3-pyridyl | 4-$CF_3$ | —$COOCH_3$ | |
| 4.16 | 4-pyridyl | 4-$CF_3$ | —$COOCH_3$ | |
| 4.17 | 2-pyridyl | 4-$CF_3$ | —$CH_3$ | |
| 4.18 | 3-pyridyl | 4-$CF_3$ | —$CH_3$ | |
| 4.19 | 4-pyridyl | 2-Cl, 4-$CF_3$ | —$CH_3$ | |
| 4.20 | 2-pyridyl | 2-Cl, 4-$CF_3$ | —$COOCH_3$ | |
| 4.21 | 3-pyridyl | 2-Cl, 4-$CF_3$ | —$COOCH_3$ | |
| 4.22 | 4-pyridyl | 2-Cl, 4-$CF_3$ | —$COOCH_3$ | |
| 4.23 | 2-pyridyl | 2-Cl, 4-$CF_3$ | —$CH_3$ | |
| 4.24 | 3-pyridyl | 2-Cl, 4-$CF_3$ | —$CH_3$ | |
| 4.25 | 4-pyridyl | 2-Cl, 4-$CF_3$ | —$CH_3$ | |
| 4.26 | 2-naphthyl | 4-Cl | H | |
| 4.27 | 3-naphthyl | 4-Cl | H | |
| 4.28 | 2-naphthyl | 4-CN | H | |
| 4.29 | 3-naphthyl | 4-CN | H | |
| 4.30 | 2-naphthyl | 4-$CF_3$ | H | |
| 4.31 | 3-naphthyl | 4-$CF_3$ | H | |
| 4.32 | 2-naphthyl | 4-$CF_3$ | —$COOCH_3$ | |
| 4.33 | 3-naphthyl | 4-$CF_3$ | —$COOCH_3$ | |
| 4.34 | 2-naphthyl | 2-Cl, 4-$CF_3$ | —$CH_3$ | |
| 4.35 | 3-naphthyl | 2-Cl, 4-$CF_3$ | —$CH_3$ | |

Example H10

4-{1-[(2-chloro-4-trifuoromethylphenyl)hydrazono]-2,2,2-trifluoroethyl}chlorobenzene

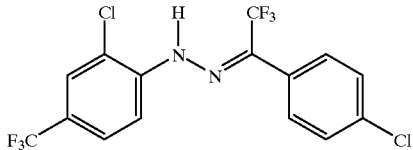

3.15 g of 2-chloro-4-trifluoromethylphenylhydrazine, 3.75 g of 2',2',2'-trifluoro-4-chloroacetophenone, 60 ml of anhydrous ethanol and 0.2 ml of glacial acetic acid are heated for two days in a water separator. The mixture is poured into 300 ml of ice-water and extracted three times using in each case 100 ml of ethyl acetate. The combined organic phases are washed with water, dried over sodium sulfate and evaporated to dryness in vacuo. The residue is crystallized from toluene/hexane 1:1. This gives the liquid title compound; $n_D^{20}$: 1.5390 (compound no. 5.2).

Example H11

The other compounds listed in Table 5 can also be prepared analogously to the procedure described in Example H10.

TABLE 5

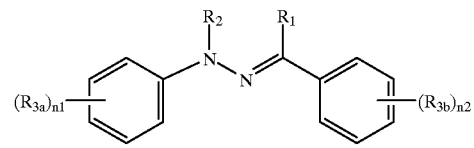

| No. | $(R_{3a})_{n1}$ | $(R_{3b})_{n2}$ | $R_1$ | $R_2$ | Physical Data |
|---|---|---|---|---|---|
| 5.1 | 2-Cl, 4-$CF_3$ | H | $CF_3$ | H | $n_D^{20}$: 1.5308 |
| 5.2 | 2-Cl, 4-$CF_3$ | 4-Cl | $CF_3$ | H | $n_D^{20}$: 1.5390 |
| 5.3 | 2,6-$Cl_2$, 4-$CF_3$ | 4-Cl | $CF_3$ | H | m.p. 66.5–67.5° C. |
| 5.4 | 2,6-$Cl_2$ | 4-Cl | $CF_3$ | H | |
| 5.5 | 2,6-$Cl_2$, 4-$CF_3$ | 4-CN | $CF_3$ | H | |
| 5.6 | 2,6-$Cl_2$, 4-$CF_3$ | 4-Cl | $CF_3$ | $CH_3$ | |
| 5.7 | 2-Cl, 4-$CF_3$ | 4-Cl | $CF_3$ | $CH_3$ | |
| 5.8 | 2,6-$Cl_2$, 4-$CF_3$ | 4-Cl | $CF_3$ | $COOCH_3$ | |
| 5.9 | 2,6-$Cl_2$, 4-$CF_3$ | CN | —C(=S)$NH_2$ | H | |
| 5.10 | 2,6-$Cl_2$, 4-$CF_3$ | CN | —C(=S)$NH_2$ | $CH_3$ | |
| 5.11 | 2,6-$Cl_2$, 4-$CF_3$ | 4-$NO_2$ | —C(=S)$NH_2$ | H | |
| 5.12 | 2,6-$Cl_2$, 4-$CF_3$ | 4-$NO_2$ | —C(=S)$NH_2$ | —$CH_3$ | |
| 5.13 | 2,6-$Cl_2$, 4-$CF_3$ | 4-$NO_2$ | —C(=S)$NH_2$ | —$CH_2OC_2H_5$ | m.p. 129–132° C. |
| 5.14 | 2,6-$Cl_2$, 4-$CF_3$ | 4-$NO_2$ | —C(=S)$NH_2$ | —$CO_2C_2H_5$ | |
| 5.15 | 2,6-$Cl_2$, 4-$CF_3$ | 4-$NO_2$ | —C(=S)$NH_2$ | —$CH_2N(CH_3)CO_2C_2H_5$ | |
| 5.16 | 2,6-$Cl_2$, 4-$CF_3$ | 4-CN | —C(=S)$NH_2$ | —$CH_2OC_2H_5$ | |
| 5.17 | 2,6-$Cl_2$, 4-$CF_3$ | 4-CN | —C(=S)$NH_2$ | —$CO_2C_2H_5$ | |

TABLE 5-continued

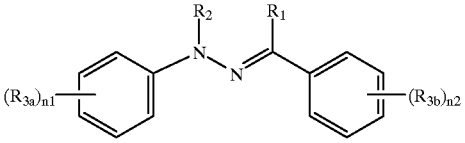

| No. | $(R_{3a})_{n1}$ | $(R_{3b})_{n2}$ | $R_1$ | $R_2$ | Physical Data |
|---|---|---|---|---|---|
| 5.18 | 2,6-$Cl_2$, 4-$CF_3$ | 4-CN | —C(=S)$NH_2$ | —$CH_2$N($CH_3$)$CO_2C_2H_5$ | |
| 5.19 | 2,4,6-$Cl_3$ | 4-$NO_2$ | —C(=S)$NH_2$ | H | |
| 5.20 | 2,4,6-$Cl_3$ | 4-$NO_2$ | —C(=S)$NH_2$ | —$CH_3$ | |
| 5.21 | 2,4,6-$Cl_3$ | 4-$NO_2$ | —C(=S)$NH_2$ | —$CH_2OC_2H_5$ | |
| 5.22 | 2,4,6-$Cl_3$ | 4-$NO_2$ | —C(=S)$NH_2$ | —$CO_2C_2H_5$ | |
| 5.23 | 2,4,6-$Cl_3$ | 4-$NO_2$ | —C(=S)$NH_2$ | —$CH_2$N($CH_3$)$CO_2C_2H_5$ | |
| 5.24 | 2,4,6-$Cl_3$ | 4-CN | —C(=S)$NH_2$ | —$CH_2OC_2H_5$ | |
| 5.25 | 2,4,6-$Cl_3$ | 4-CN | —C(=S)$NH_2$ | —$CO_2C_2H_5$ | |
| 5.26 | 2,4,6-$Cl_3$ | 4-CN | —C(=S)$NH_2$ | —$CH_2$N($CH_3$)$CO_2C_2H_5$ | |
| 5.27 | 2,6-$Cl_2$, 4-$CF_3$ | 4-$NO_2$ | —$CF_3$ | H | |
| 5.28 | 2,6-$Cl_2$, 4-$CF_3$ | 4-$NO_2$ | —$CF_3$ | —$CH_3$ | |
| 5.29 | 2,6-$Cl_2$, 4-$CF_3$ | 4-$NO_2$ | —$CF_3$ | —$CH_2OC_2H_5$ | |
| 5.30 | 2,6-$Cl_2$, 4-$CF_3$ | 4-$NO_2$ | —$CF_3$ | —$CO_2C_2H_5$ | |
| 5.31 | 2,6-$Cl_2$, 4-$CF_3$ | 4-$NO_2$ | —$CF_3$ | —$CH_2$N($CH_3$)$CO_2C_2H_5$ | |
| 5.32 | 2,6-$Cl_2$, 4-$CF_3$ | —CN | —$CF_3$ | —$CH_3$ | |
| 5.33 | 2,6-$Cl_2$, 4-$CF_3$ | —CN | —$CF_3$ | —$CH_2OC_2H_5$ | |
| 5.34 | 2,6-$Cl_2$, 4-$CF_3$ | —CN | —$CF_3$ | —$CO_2C_2H_5$ | |
| 5.35 | 2,6-$Cl_2$, 4-$CF_3$ | —CN | —$CF_3$ | —$CH_2$N($CH_3$)$CO_2C_2H_5$ | |

Example H12

The compounds listed in Tables 6 to 29 can also be prepared analogously to the procedure described in Examples H5 to H11.

TABLE A

| No | $R_2$ | $(R_{3b})_{n2}$ |
|---|---|---|
| A.1) | H | 4-CN |
| A.2) | H | 4-$NO_2$ |
| A.3) | H | 4-$CF_3$ |
| A.4) | H | 2-Cl, 4-$NO_2$ |
| A.5) | H | 3-$CH_3$, 4-$NO_2$ |
| A.6) | H | 4-$C_6H_5$ |
| A.7) | H | 4-$C_6H_4$-4-Cl |
| A.8) | H | 4-$C_6H_3$-2,4-$Cl_2$ |
| A.9) | H | 4-$C_6H_4$-4-$CF_3$ |
| A.10) | H | 4-$C_6H_4$-3-$CF_3$ |
| A.11) | H | 4-$C_6H_3$-3,4-$Cl_2$ |
| A.12) | H | 2-F-4-CN |
| A.13) | H | 2-F, 4-$NO_2$ |
| A.14) | H | 4-$COCF_3$ |
| A.15) | H | 4-CHO |
| A.16) | H | 4-Cl, 3-$NO_2$ |
| A.17) | —$CH_3$ | 4-CN |
| A.18) | —$CH_3$ | 4-$NO_2$ |
| A.19) | —$CH_3$ | 4-$CF_3$ |
| A.20) | —$CH_3$ | 2-Cl, 4-$NO_2$ |
| A.21) | —$CH_3$ | 3-$CH_3$, 4-$NO_2$ |
| A.22) | —$CH_3$ | 4-$C_6H_5$ |
| A.23) | —$CH_3$ | 4-$C_6H_4$, 4-Cl |
| A.24) | —$CH_3$ | 4-$C_6H_3$-2,4-$Cl_2$ |
| A.25) | —$CH_3$ | 4-$C_6H_4$-4-$CF_3$ |
| A.26) | —$CH_3$ | 4-$C_6H_4$-3-$CF_3$ |
| A.27) | —$CH_3$ | 4-$C_6H_3$-3,4-$Cl_2$ |
| A.28) | —$CH_3$ | 2-F, 4-CN |
| A.29) | —$CH_3$ | 2-F, 4-$NO_2$ |
| A.30) | —$CH_3$ | 4-$COCF_3$ |
| A.31) | —$CH_3$ | 4-CHO |
| A.32) | —$CH_3$ | 4-Cl, 3-$NO_2$ |
| A.33) | —$C_2H_5$ | 4-CN |
| A.34) | —$C_2H_5$ | 4-$NO_2$ |
| A.35) | —$C_2H_5$ | 4-$CF_3$ |
| A.36) | —$C_2H_5$ | 2-Cl, 4-$NO_2$ |

TABLE A-continued

| No | $R_2$ | $(R_{3b})_{n2}$ |
|---|---|---|
| A.37) | —$C_2H_5$ | 3-$CH_3$, 4-$NO_2$ |
| A.38) | —$C_2H_5$ | 4-$C_6H_5$ |
| A.39) | —$C_2H_5$ | 4-$C_6H_4$-4-Cl |
| A.40) | —$C_2H_5$ | 4-$C_6H_3$-2,4-$Cl_2$ |
| A.41) | —$C_2H_5$ | 4-$C_6H_4$-4-$CF_3$ |
| A.42) | —$C_2H_5$ | 4-$C_6H_4$-3-$CF_3$ |
| A.43) | —$C_2H_5$ | 4-$C_6H_3$-3,4-$Cl_2$ |
| A.44) | —$C_2H_5$ | 2-F, 4-CN |
| A.45) | —$C_2H_5$ | 2-F, 4-$NO_2$ |
| A.46) | —$C_2H_5$ | 4-$COCF_3$ |
| A.47) | —$C_2H_5$ | 4-CHO |
| A.48) | —$C_2H_5$ | 4-Cl, 3-$NO_2$ |
| A.49) | —$CH_2OC_2H_5$ | 4-CN |
| A.50) | —$CH_2OC_2H_5$ | 4-$NO_2$ |
| A.51) | —$CH_2OC_2H_5$ | 4-$CF_3$ |
| A.52) | —$CH_2OC_2H_5$ | 2-Cl, 4-$NO_2$ |
| A.53) | —$CH_2OC_2H_5$ | 3-$CH_3$, 4-$NO_2$ |
| A.54) | —$CH_2OC_2H_5$ | 4-$C_6H_5$ |
| A.55) | —$CH_2OC_2H_5$ | 4-$C_6H_4$-4-Cl |
| A.56) | —$CH_2OC_2H_5$ | 4-$C_6H_3$-2,4-$Cl_2$ |
| A.57) | —$CH_2OC_2H_5$ | 4-$C_6H_4$-4-$CF_3$ |
| A.58) | —$CH_2OC_2H_5$ | 4-$C_6H_4$-3-$CF_3$ |
| A.59) | —$CH_2OC_2H_5$ | 4-$C_6H_3$-3,4-$Cl_2$ |
| A.60) | —$CH_2OC_2H_5$ | 2-F, 4-CN |
| A.61) | —$CH_2OC_2H_5$ | 2-F, 4-$NO_2$ |
| A.62) | —$CH_2OC_2H_5$ | 4-$COCF_3$ |
| A.63) | —$CH_2OC_2H_5$ | 4-CHO |
| A.64) | —$CH_2OC_2H_5$ | 4-Cl, 3-$NO_2$ |
| A.65) | —$CH_2OCH_3$ | 4-CN |
| A.66) | —$CH_2OCH_3$ | 4-$NO_2$ |
| A.67) | —$CH_2OCH_3$ | 4-$CF_3$ |
| A.68) | —$CH_2OCH_3$ | 2-Cl, 4-$NO_2$ |
| A.69) | —$CH_2OCH_3$ | 3-$CH_3$, 4-$NO_2$ |
| A.70) | —$CH_2OCH_3$ | 4-$C_6H_5$ |
| A.71) | —$CH_2OCH_3$ | 4-$C_6H_4$-4-Cl |
| A.72) | —$CH_2OCH_3$ | 4-$C_6H_3$-2,4-$Cl_2$ |
| A.73) | —$CH_2OCH_3$ | 4-$C_6H_4$-4-$CF_3$ |
| A.74) | —$CH_2OCH_3$ | 4-$C_6H_4$-3-$CF_3$ |
| A.75) | —$CH_2OCH_3$ | 4-$C_6H_3$-3,4-$Cl_2$ |
| A.76) | —$CH_2OCH_3$ | 2-F, 4-CN |
| A.77) | —$CH_2OCH_3$ | 2-F, 4-$NO_2$ |
| A.78) | —$CH_2OCH_3$ | 4-$COCF_3$ |

TABLE A-continued

| No | $R_2$ | $(R_{3b})_{n2}$ |
|---|---|---|
| A.79) | —CH$_2$OCH$_3$ | 4-CHO |
| A.80) | —CH$_2$OCH$_3$ | 4-Cl, 3-NO$_2$ |
| A.81) | —CN | 4-CN |
| A.82) | —CN | 4-NO$_2$ |
| A.83) | —CN | 4-CF$_3$ |
| A.84) | —CN | 2-Cl, 4-NO$_2$ |
| A.85) | —CN | 3-CH$_3$, 4-NO$_2$ |
| A.86) | —CN | 4-C$_6$H$_5$ |
| A.87) | —CN | 4-C$_6$H$_4$-4-Cl |
| A.88) | —CN | 4-C$_6$H$_3$-2,4-Cl$_2$ |
| A.89) | —CN | 4-C$_6$H$_4$-4-CF$_3$ |
| A.90) | —CN | 4-C$_6$H$_4$-3-CF$_3$ |
| A.91) | —CN | 4-C$_6$H$_3$-3,4-Cl$_2$ |
| A.92) | —CN | 2-F, 4-CN |
| A.93) | —CN | 2-F, 4-NO$_2$ |
| A.94) | —CN | 4-COCF$_3$ |
| A.95) | —CN | 4-CHO |
| A.96) | —CN | 4-Cl, 3-NO$_2$ |
| A.97) | —COCH$_3$ | 4-CN |
| A.98) | —COCH$_3$ | 4-NO$_2$ |
| A.99) | —COCH$_3$ | 4-CF$_3$ |
| A.100) | —COCH$_3$ | 2-Cl, 4-NO$_2$ |
| A.101) | —COCH$_3$ | 3-CH$_3$, 4-NO$_2$ |
| A.102) | —COCH$_3$ | 4-C$_6$H$_5$ |
| A.103) | —COCH$_3$ | 4-C$_6$H$_4$-4-Cl |
| A.104) | —COCH$_3$ | 4-C$_6$H$_3$-2,4-Cl$_2$ |
| A.105) | —COCH$_3$ | 4-C$_6$H$_4$-4-CF$_3$ |
| A.106) | —COCH$_3$ | 4-C$_6$H$_4$-3-CF$_3$ |
| A.107) | —COCH$_3$ | 4-C$_6$H$_3$-3,4-Cl$_2$ |
| A.108) | —COCH$_3$ | 2-F, 4-CN |
| A.109) | —COCH$_3$ | 2-F, 4-NO$_2$ |
| A.110) | —COCH$_3$ | 4-COCF$_3$ |
| A.111) | —COCH$_3$ | 4-CHO |
| A.112) | —COCH$_3$ | 4-Cl, 3-NO$_2$ |
| A.113) | —CH$_2$—CH=CH$_2$ | 4-CN |
| A.114) | —CH$_2$—CH=CH$_2$ | 4-NO$_2$ |
| A.115) | —CH$_2$—CH=CH$_2$ | 4-CF$_3$ |
| A.116) | —CH$_2$—CH=CH$_2$ | 2-Cl, 4-NO$_2$ |
| A.117) | —CH$_2$—CH=CH$_2$ | 3-CH$_3$, 4-NO$_2$ |
| A.118) | —CH$_2$—CH=CH$_2$ | 4-C$_6$H$_5$ |
| A.119) | —CH$_2$—CH=CH$_2$ | 4-C$_6$H$_4$-4-Cl |
| A.120) | —CH$_2$—CH=CH$_2$ | 4-C$_6$H$_3$-2,4-Cl$_2$ |
| A.121) | —CH$_2$—CH=CH$_2$ | 4-C$_6$H$_4$-4-CF$_3$ |
| A.122) | —CH$_2$—CH=CH$_2$ | 4-C$_6$H$_4$-3-CF$_3$ |
| A.123) | —CH$_2$—CH=CH$_2$ | 4-C$_6$H$_3$-3,4-Cl$_2$ |
| A.124) | —CH$_2$—CH=CH$_2$ | 2-F, 4-CN |
| A.125) | —CH$_2$—CH=CH$_2$ | 2-F, 4-NO$_2$ |
| A.126) | —CH$_2$—CH=CH$_2$ | 4-COCF$_3$ |
| A.127) | —CH$_2$—CH=CH$_2$ | 4-CHO |
| A.128) | —CH$_2$—CH=CH$_2$ | 4-Cl, 3-NO$_2$ |
| A.129) | —CH$_2$C≡CH | 4-CN |
| A.130) | —CH$_2$C≡CH | 4-NO$_2$ |
| A.131) | —CH$_2$C≡CH | 4-CF$_3$ |
| A.132) | —CH$_2$C≡CH | 2-Cl, 4-NO$_2$ |
| A.133) | —CH$_2$C≡CH | 3-CH$_3$, 4-NO$_2$ |
| A.134) | —CH$_2$C≡CH | 4-C$_6$H$_5$ |
| A.135) | —CH$_2$C≡CH | 4-C$_6$H$_4$-4-Cl |
| A.136) | —CH$_2$C≡CH | 4-C$_6$H$_3$-2,4-Cl$_2$ |
| A.137) | —CH$_2$C≡CH | 4-C$_6$H$_4$-4-CF$_3$ |
| A.138) | —CH$_2$C≡CH | 4-C$_6$H$_4$-3-CF$_3$ |
| A.139) | —CH$_2$C≡CH | 4-C$_6$H$_3$-3,4-Cl$_2$ |
| A.140) | —CH$_2$C≡CH | 2-F, 4-CN |
| A.141) | —CH$_2$C≡CH | 2-F, 4-NO$_2$ |
| A.142) | —CH$_2$C≡CH | 4-COCF$_3$ |
| A.143) | —CH$_2$C≡CH | 4-CHO |
| A.144) | —CH$_2$C≡CH | 4-Cl, 3-NO$_2$ |
| A.145) | —CO$_2$CH$_3$ | 4-CN |
| A.146) | —CO$_2$CH$_3$ | 4-NO$_2$ |
| A.147) | —CO$_2$CH$_3$ | 4-CF$_3$ |
| A.148) | —CO$_2$CH$_3$ | 2-Cl, 4-NO$_2$ |
| A.149) | —CO$_2$CH$_3$ | 3-CH$_3$, 4-NO$_2$ |
| A.150) | —CO$_2$CH$_3$ | 4-C$_6$H$_5$ |
| A.151) | —CO$_2$CH$_3$ | 4-C$_6$H$_4$-4-Cl |
| A.152) | —CO$_2$CH$_3$ | 4-C$_6$H$_3$-2,4-Cl$_2$ |
| A.153) | —CO$_2$CH$_3$ | 4-C$_6$H$_4$-4-CF$_3$ |
| A.154) | —CO$_2$CH$_3$ | 4-C$_6$H$_4$-3-CF$_3$ |
| A.155) | —CO$_2$CH$_3$ | 4-C$_6$H$_3$-3,4-Cl$_2$ |
| A.156) | —CO$_2$CH$_3$ | 2-F, 4-CN |
| A.157) | —CO$_2$CH$_3$ | 2-F, 4-NO$_2$ |
| A.158) | —CO$_2$CH$_3$ | 4-COCF$_3$ |
| A.159) | —CO$_2$CH$_3$ | 4-CHO |
| A.160) | —CO$_2$CH$_3$ | 4-Cl, 3-NO$_2$ |
| A.161) | —CO$_2$C$_2$H$_5$ | 4-CN |
| A.162) | —CO$_2$C$_2$H$_5$ | 4-NO$_2$ |
| A.163) | —CO$_2$C$_2$H$_5$ | 4-CF$_3$ |
| A.164) | —CO$_2$C$_2$H$_5$ | 2-Cl, 4-NO$_2$ |
| A.165) | —CO$_2$C$_2$H$_5$ | 3-CH$_3$, 4-NO$_2$ |
| A.166) | —CO$_2$C$_2$H$_5$ | 4-C$_6$H$_5$ |
| A.167) | —CO$_2$C$_2$H$_5$ | 4-C$_6$H$_4$-4-Cl |
| A.168) | —CO$_2$C$_2$H$_5$ | 4-C$_6$H$_3$-2,4-Cl$_2$ |
| A.169) | —CO$_2$C$_2$H$_5$ | 4-C$_6$H$_4$-4-CF$_3$ |
| A.170) | —CO$_2$C$_2$H$_5$ | 4-C$_6$H$_4$-3-CF$_3$ |
| A.171) | —CO$_2$C$_2$H$_5$ | 4-C$_6$H$_3$-3,4-Cl$_2$ |
| A.172) | —CO$_2$C$_2$H$_5$ | 2-F, 4-CN |
| A.173) | —CO$_2$C$_2$H$_5$ | 2-F, 4-NO$_2$ |
| A.174) | —CO$_2$C$_2$H$_5$ | 4-COCF$_3$ |
| A.175) | —CO$_2$C$_2$H$_5$ | 4-CHO |
| A.176) | —CO$_2$C$_2$H$_5$ | 4-Cl, 3-NO$_2$ |
| A.177) | —CH$_2$N(CH$_3$)CO$_2$C$_2$H$_5$ | 4-CN |
| A.178) | —CH$_2$N(CH$_3$)CO$_2$C$_2$H$_5$ | 4-NO$_2$ |
| A.179) | —CH$_2$N(CH$_3$)CO$_2$C$_2$H$_5$ | 4-CF$_3$ |
| A.180) | —CH$_2$N(CH$_3$)CO$_2$C$_2$H$_5$ | 2-Cl, 4-NO$_2$ |
| A.181) | —CH$_2$N(CH$_3$)CO$_2$C$_2$H$_5$ | 3-CH$_3$, 4-NO$_2$ |
| A.182) | —CH$_2$N(CH$_3$)CO$_2$C$_2$H$_5$ | 4-C$_6$H$_5$ |
| A.183) | —CH$_2$N(CH$_3$)CO$_2$C$_2$H$_5$ | 4-C$_6$H$_4$-4-Cl |
| A.184) | —CH$_2$N(CH$_3$)CO$_2$C$_2$H$_5$ | 4-C$_6$H$_3$-2,4-Cl$_2$ |
| A.185) | —CH$_2$N(CH$_3$)CO$_2$C$_2$H$_5$ | 4-C$_6$H$_4$-4-CF$_3$ |
| A.186) | —CH$_2$N(CH$_3$)CO$_2$C$_2$H$_5$ | 4-C$_6$H$_4$-3-CF$_3$ |
| A.187) | —CH$_2$N(CH$_3$)CO$_2$C$_2$H$_5$ | 4-C$_6$H$_3$-3,4-Cl$_2$ |
| A.188) | —CH$_2$N(CH$_3$)CO$_2$C$_2$H$_5$ | 2-F, 4-CN |
| A.189) | —CH$_2$N(CH$_3$)CO$_2$C$_2$H$_5$ | 2-F, 4-NO$_2$ |
| A.190) | —CH$_2$N(CH$_3$)CO$_2$C$_2$H$_5$ | 4-COCF$_3$ |
| A.191) | —CH$_2$N(CH$_3$)CO$_2$C$_2$H$_5$ | 4-CHO |
| A.192) | —CH$_2$N(CH$_3$)CO$_2$C$_2$H$_5$ | 4-Cl, 3-NO$_2$ |
| A.193) | —CH$_2$N(CH$_3$)CO$_2$CH$_3$ | 4-CN |
| A.194) | —CH$_2$N(CH$_3$)CO$_2$CH$_3$ | 4-NO$_2$ |
| A.195) | —CH$_2$N(CH$_3$)CO$_2$CH$_3$ | 4-CF$_3$ |
| A.196) | —CH$_2$N(CH$_3$)CO$_2$CH$_3$ | 2-Cl, 4-NO$_2$ |
| A.197) | —CH$_2$N(CH$_3$)CO$_2$CH$_3$ | 3-CH$_3$, 4-NO$_2$ |
| A.198) | —CH$_2$N(CH$_3$)CO$_2$CH$_3$ | 4-C$_6$H$_5$ |
| A.199) | —CH$_2$N(CH$_3$)CO$_2$CH$_3$ | 4-C$_6$H$_4$-4-Cl |
| A.200) | —CH$_2$N(CH$_3$)CO$_2$CH$_3$ | 4-C$_6$H$_3$-2,4-Cl$_2$ |
| A.201) | —CH$_2$N(CH$_3$)CO$_2$CH$_3$ | 4-C$_6$H$_4$-4-CF$_3$ |
| A.202) | —CH$_2$N(CH$_3$)CO$_2$CH$_3$ | 4-C$_6$H$_4$-3-CF$_3$ |
| A.203) | —CH$_2$N(CH$_3$)CO$_2$CH$_3$ | 4-C$_6$H$_3$-3,4-Cl$_2$ |
| A.204) | —CH$_2$N(CH$_3$)CO$_2$CH$_3$ | 2-F, 4-CN |
| A.205) | —CH$_2$N(CH$_3$)CO$_2$CH$_3$ | 2-F, 4-NO$_2$ |
| A.206) | —CH$_2$N(CH$_3$)CO$_2$CH$_3$ | 4-COCF$_3$ |
| A.207) | —CH$_2$N(CH$_3$)CO$_2$CH$_3$ | 4-CHO |
| A.208) | —CH$_2$N(CH$_3$)CO$_2$CH$_3$ | 4-Cl, 3-NO$_2$ |
| A.209) | —COCO$_2$C$_2$H$_5$ | 4-CN |
| A.210) | —COCO$_2$C$_2$H$_5$ | 4-NO$_2$ |
| A.211) | —COCO$_2$C$_2$H$_5$ | 4-CF$_3$ |
| A.212) | —COCO$_2$C$_2$H$_5$ | 2-Cl, 4-NO$_2$ |
| A.213) | —COCO$_2$C$_2$H$_5$ | 3-CH$_3$, 4-NO$_2$ |
| A.214) | —COCO$_2$C$_2$H$_5$ | 4-C$_6$H$_5$ |
| A.215) | —COCO$_2$C$_2$H$_5$ | 4-C$_6$H$_4$-4-Cl |
| A.216) | —COCO$_2$C$_2$H$_5$ | 4-C$_6$H$_3$-2,4-Cl$_2$ |
| A.217) | —COCO$_2$C$_2$H$_5$ | 4-C$_6$H$_4$-4-CF$_3$ |
| A.218) | —COCO$_2$C$_2$H$_5$ | 4-C$_6$H$_4$-3-CF$_3$ |
| A.219) | —COCO$_2$C$_2$H$_5$ | 4-C$_6$H$_3$-3,4-Cl$_2$ |
| A.220) | —COCO$_2$C$_2$H$_5$ | 2-F, 4-CN |
| A.221) | —COCO$_2$C$_2$H$_5$ | 2-F, 4-NO$_2$ |
| A.222) | —COCO$_2$C$_2$H$_5$ | 4-COCF$_3$ |
| A.223) | —COCO$_2$C$_2$H$_5$ | 4-CHO |
| A.224) | —COCO$_2$C$_2$H$_5$ | 4-Cl, 3-NO$_2$ |
| A.225) | —COCONHC$_2$H$_5$ | 4-CN |
| A.226) | —COCONHC$_2$H$_5$ | 4-NO$_2$ |
| A.227) | —COCONHC$_2$H$_5$ | 4-CF$_3$ |
| A.228) | —COCONHC$_2$H$_5$ | 2-Cl, 4-NO$_2$ |
| A.229) | —COCONHC$_2$H$_5$ | 3-CH$_3$, 4-NO$_2$ |
| A.230) | —COCONHC$_2$H$_5$ | 4-C$_6$H$_5$ |
| A.231) | —COCONHC$_2$H$_5$ | 4-C$_6$H$_4$-4-Cl |
| A.232) | —COCONHC$_2$H$_5$ | 4-C$_6$H$_3$-2,4-Cl$_2$ |

TABLE A-continued

| No | $R_2$ | $(R_{3b})_{n2}$ |
|---|---|---|
| A.233) | —COCONHC$_2$H$_5$ | 4-C$_6$H$_4$-4-CF$_3$ |
| A.234) | —COCONHC$_2$H$_5$ | 4-C$_6$H$_4$-3-CF$_3$ |
| A.235) | —COCONHC$_2$H$_5$ | 4-C$_6$H$_3$-3,4-Cl$_2$ |
| A.236) | —COCONHC$_2$H$_5$ | 2-F, 4-CN |
| A.237) | —COCONHC$_2$H$_5$ | 2-F, 4-NO$_2$ |
| A.238) | —COCONHC$_2$H$_5$ | 4-COCF$_3$ |
| A.239) | —COCONHC$_2$H$_5$ | 4-CHO |
| A.240) | —COCONHC$_2$H$_5$ | 4-Cl, 3-NO$_2$ |
| A.241) | —CH$_2$N(CH$_3$)SO$_2$CH$_3$ | 4-CN |
| A.242) | —CH$_2$N(CH$_3$)SO$_2$CH$_3$ | 4-NO$_2$ |
| A.243) | —CH$_2$N(CH$_3$)SO$_2$CH$_3$ | 4-CF$_3$ |
| A.244) | —CH$_2$N(CH$_3$)SO$_2$CH$_3$ | 2-Cl, 4-NO$_2$ |
| A.245) | —CH$_2$N(CH$_3$)SO$_2$CH$_3$ | 3-CH$_3$, 4-NO$_2$ |
| A.246) | —CH$_2$N(CH$_3$)SO$_2$CH$_3$ | 4-C$_6$H$_5$ |
| A.247) | —CH$_2$N(CH$_3$)SO$_2$CH$_3$ | 4-C$_6$H$_4$-4-Cl |
| A.248) | —CH$_2$N(CH$_3$)SO$_2$CH$_3$ | 4-C$_6$H$_3$-2,4-Cl$_2$ |
| A.249) | —CH$_2$N(CH$_3$)SO$_2$CH$_3$ | 4-C$_6$H$_4$-4-CF$_3$ |
| A.250) | —CH$_2$N(CH$_3$)SO$_2$CH$_3$ | 4-C$_6$H$_4$-3-CF$_3$ |
| A.251) | —CH$_2$N(CH$_3$)SO$_2$CH$_3$ | 4-C$_6$H$_3$-3,4-Cl$_2$ |
| A.252) | —CH$_2$N(CH$_3$)SO$_2$CH$_3$ | 2-F, 4-CN |
| A.253) | —CH$_2$N(CH$_3$)SO$_2$CH$_3$ | 2-F, 4-NO$_2$ |
| A.254) | —CH$_2$N(CH$_3$)SO$_2$CH$_3$ | 4-COCF$_3$ |
| A.255) | —CH$_2$N(CH$_3$)SO$_2$CH$_3$ | 4-CHO |
| A.256) | —CH$_2$N(CH$_3$)SO$_2$CH$_3$ | 4-Cl, 3-NO$_2$ |
| A.257) | —CH$_2$Cl | 4-CN |
| A.258) | —CH$_2$Cl | 4-NO$_2$ |
| A.259) | —CH$_2$Cl | 4-CF$_3$ |
| A.260) | —CH$_2$Cl | 2-Cl, 4-NO$_2$ |
| A.261) | —CH$_2$Cl | 3-CH$_3$, 4-NO$_2$ |
| A.262) | —CH$_2$Cl | 4-C$_6$H$_5$ |
| A.263) | —CH$_2$Cl | 4-C$_6$H$_4$-4-Cl |
| A.264) | —CH$_2$Cl | 4-C$_6$H$_3$-2,4-Cl$_2$ |
| A.265) | —CH$_2$Cl | 4-C$_6$H$_4$-4-CF$_3$ |
| A.266) | —CH$_2$Cl | 4-C$_6$H$_4$-3-CF$_3$ |
| A.267) | —CH$_2$Cl | 4-C$_6$H$_3$-3,4-Cl$_2$ |
| A.268) | —CH$_2$Cl | 2-F, 4-CN |
| A.269) | —CH$_2$Cl | 2-F, 4-NO$_2$ |
| A.270) | —CH$_2$Cl | 4-COCF$_3$ |
| A.271) | —CH$_2$Cl | 4-CHO |
| A.272) | —CH$_2$Cl | 4-Cl, 3-NO$_2$ |

Table 6

Compounds of the general formula

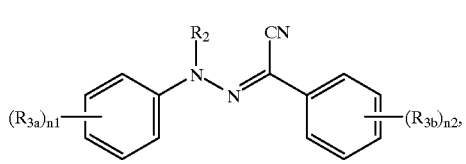

(Ic)

in which $(R_{3a})_{n1}$ is 2,6-Cl$_2$-4-CF$_3$ and $R_2$ and $(R_{3b})_{n2}$ correspond to one line of Table A.

Table 7

Compounds of the general formula (Ic), in which $(R_{3a})_{n1}$ is 2,4,6-Cl$_3$ and $R_2$ and $(R_{3b})_{n2}$ correspond to one line of Table A.

Table 8

Compounds of the general formula (Ic), in which $(R_{3a})_{n1}$ is 2-Cl-4-CF$_3$ and $R_2$ and $(R_{3b})_n$ correspond to one line of Table A.

Table 9

Compounds of the general formula (Ic), in which $(R_{3a})_{n1}$ is 2,6-Cl$_2$-4-NO$_2$ and $R_2$ and $(R_{3b})_{n2}$ correspond to one line of Table A.

Table 10

Compounds of the general formula (Ic), in which $(R_{3a})_{n1}$ is 2,6-Cl$_2$-4-OCF$_3$ and $R_2$ and $(R_{3b})_{n2}$ correspond to one line of Table A.

Table 11

Compounds of the general formula (Ic), in which $(R_{3a})_{n1}$ is 2,6-Cl$_2$-4-F and $R_2$ and $(R_{3b})_{n2}$ correspond to one line of Table A.

Table 12

Compounds of the general formula (Ic), in which $(R_{3a})_{n1}$ is 2,6-Cl$_2$-4-Br and $R_2$ and $(R_{3b})_{n2}$ correspond to one line of Table A.

Table 13

Compounds of the general formula (Ic), in which $(R_{3a})_{n1}$ is 2-Cl-4-CF$_3$-6-F and $R_2$ and $(R_{3b})_{n2}$ correspond to one line of Table A.

Table 14

Compounds of the general formula (Ic), in which $(R_{3a})_{n1}$ is 2,3,6-Cl$_3$-4-CF$_3$ and $R_2$ and $(R_{3b})_{n2}$ correspond to one line of Table A.

Table 15

Compounds of the general formula (Ic), in which $(R_{3a})_{n1}$ is 2,6-Cl$_2$-3-F-4-CF$_3$ and $R_2$ and $(R_{3b})_{n2}$ correspond to one line of Table A.

Table 16

Compounds of the general formula (Ic), in which $(R_{3a})_{n1}$ is 2,3-F$_2$-4-CF$_3$-6-Cl and $R_2$ and $(R_{3b})_{n2}$ correspond to one line of Table A.

Table 17

Compounds of the general formula (Ic), in which $(R_{3a})_{n1}$ is 2,6-Cl$_2$-4-CN and $R_2$ and $(R_{3b})_{n2}$ correspond to one line of Table A.

Table 18

Compounds of the general formula (Ic), in which $(R_{3a})_{n1}$ is 2,4-Cl$_2$-6-CF$_3$ and $R_2$ and $(R_{3b})_{n2}$ correspond to one line of Table A.

Table 19

Compounds of the general formula (Ic), in which $(R_{3a})_{n1}$ is 2,6-Cl$_2$-4-SCF$_3$ and $R_2$ and $(R_{3b})_{n2}$ correspond to one line of Table A.

Table 20

Compounds of the general formula (Ic), in which $(R_{3a})_{n1}$ is 2,6-Cl$_2$-4-SOCF$_3$ and $R_2$ and $(R_{3b})_{n2}$ correspond to one line of Table A.

Table 21

Compounds of the general formula (Ic), in which $(R_{3a})_{n1}$ is 2,6-Cl$_2$-4-SO$_2$CF$_3$ and $R_2$ and $(R_{3b})_{n2}$ correspond to one line of Table A.

Table 22

Compounds of the general formula (Ic), in which $(R_{3a})_{n1}$ is 2,6-Cl$_2$-4-SO$_2$CH$_3$ and $R_2$ and $(R_{3b})_{n2}$ correspond to one line of Table A.

Table 23

Compounds of the general formula (Ic), in which $(R_{3a})_{n1}$ is 2,6-$Cl_2$-4-$OCF_2Br$ and $R_2$ and $(R_{3b})_{n2}$ correspond to one line of Table A.

Table 24

Compounds of the general formula (Ic), in which $(R_{3a})_{n1}$ is 2,6-$Cl_2$-4-$OCF_2H$ and $R_2$ and $(R_{3b})_{n2}$ correspond to one line of Table A.

Table 25

Compounds of the general formula (Ic), in which $(R_{3a})_{n1}$ is 2,6-$Cl_2$-4-$C_2F_5$ and $R_2$ and $(R_{3b})_{n2}$ correspond to one line of Table A.

Table 26

Compounds of the general formula (Ic), in which $(R_{3a})_{n1}$ is 2,6-$(NO_2)_2$-4-$CF_3$ and $R_2$ and $(R_{3b})_{n2}$ correspond to one line of Table A.

Table 27

Compounds of the general formula (Ic), in which $(R_{3a})_{n1}$ is 2,6-$(NO_2)_2$-4-Cl and $R_2$ and $(R_{3b})_{n2}$ correspond to one line of Table A.

Table 28

Compounds of the general formula (Ic), in which $(R_{3a})_{n1}$ is 2,6-$Cl_2$-4-$OSO_2CH_3$ and $R_2$ and $(R_{3b})_{n2}$ correspond to one line of Table A.

Table 29

Compounds of the general formula (Ic), in which $(R_{3a})_{n1}$ is 2,6-$Cl_2$-4-$OSO_2CF_3$ and $R_2$ and $(R_{3b})_{n2}$ correspond to one line of Table A.

FORMULATION EXAMPLES (%=percent by weight)

EXAMPLE F1

| Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | — | 12% |
| Cyclohexanone | — | 15% | 20% |
| Xylene mixture | 65% | 25% | 20% |

EO is the degree of ethoxylation of the alcoholic group in question.

Mixing finely ground active ingredient and additives gives an emulsion concentrate which gives emulsions of any desired concentration by dilution with water.

EXAMPLE F2

| Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol (molecular weight 400) | — | 70% | — | — |
| N-Methylpyrrolid-2-one | — | 20% | — | — |
| Epoxidized coconut oil | — | — | 1% | 5% |
| Petroleum ether (boiling range: 160–190) | — | — | 94% | — |

Mixing finely ground active ingredient and additives gives a solution which is suitable for use in the form of microdrops.

EXAMPLE F3

| Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier mixture, and the solvent is evaporated in vacuo.

EXAMPLE F4

| Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by mixing active ingredient and carriers.

EXAMPLE F5

| Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenol polyethylene glycol ether (7–8 mol of EO) | — | 2% | — |
| Highly disperse silica | 5% | 10% | 10% |
| Kaolin | 62% | 27% | — |

Active ingredient and additives are mixed and the mixture is ground in a suitable mill. This gives wettable powders which can be diluted with water to give suspensions of any desired concentration.

EXAMPLE F6

| Emulsion concentrate | |
|---|---|
| Active ingredient | 10% |
| Octylphenol polyethylene glycol ether (4–5 mol of EO) | 3% |
| Calcium dodecylbenzenesulfonate | 3% |
| Castor oil polyethylene glycol ether (36 mol of EO) | 4% |
| Cyclohexanone | 30% |
| Xylene mixture | 50% |

An emulsion concentrate, which gives emulsions of any desired concentration by dilution with water, is obtained by mixing finely ground active ingredient and additives.

EXAMPLE F7

| Dusts | a) | b) |
|---|---|---|
| Active ingredient | 5% | 8% |
| Talc | 95% | — |
| Kaolin | — | 92% |

Ready-to-use dusts are obtained by mixing active ingredient and carrier and grinding the mixture in a suitable mill.

EXAMPLE F8

| Extruder granules | |
|---|---|
| Active ingredient | 10% |
| Sodium lignosulfonate | 2% |
| Carboxymethylcellulose | 1% |
| Kaolin | 87% |

Active ingredient and additives are mixed, the mixture is ground, the powder is moistened with water, extruded and granulated, and the granules are dried in a stream of air.

EXAMPLE F9

| Coated granules | |
|---|---|
| Active ingredient | 3% |
| Polyethylene glycol (MW 200) | 3% |
| Kaolin | 94% |

Dust-free coated granules are obtained by uniformly applying the finely ground active ingredient, in a mixer, to the kaolin which has been moistened with polyethylene glycol.

EXAMPLE F10

| Suspension concentrate | |
|---|---|
| Active ingredient | 40% |
| Ethylene glycol | 10% |
| Nonylphenol polyethylene glycol ether (15 mol of EO) | 6% |
| Sodium lignosulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

A suspension concentrate, which gives suspensions of any desired concentration by dilution with water, is obtained by mixing finely ground active ingredient and additives.

Biological Examples

Example B1

Ovicidal Action on *Heliothis virescens*

*Heliothis virescens* eggs which have been deposited on filter paper are briefly immersed into an acetonic/aqueous test solution comprising 400 ppm of the active ingredient to be tested. After the test solution has dried on, the eggs are incubated in Petri dishes. After 6 days, the percentage hatching rate of the eggs is evaluated in comparison with untreated control batches (% reduction in hatching).

In this test, compounds of Tables 3 to 29 are very effective. Compounds nos. 3.2 to 3.4, 3.18, 3.20, 3.26, 3.43, 3.48, 3.50, 3.54, 3.77 to 3.85, 3.90 to 3.98 and 3.101 to 3.103, in particular, exhibit an activity of over 80%.

Example B2

Action Against *Spodoptera littoralis* Caterpillars

Young soya plants are sprayed with an aqueous emulsion spray mixture which comprises 400 ppm of the active ingredient. After the spray coating has dried on, the soya plants are populated with 10 third instar caterpillars of *Spodoptera littoralis* and introduced into a plastic container. Three days later, the test is evaluated. The percentage reduction in population, or the percentage reduction in feeding damage (% activity), is determined by comparing the number of dead caterpillars and the feeding damage on the treated plants with those on the untreated plants.

In this test, compounds of Tables 3 to 29 are very effective. Compounds nos. 3.2 to 3.4, 3.10, 3.18, 3.20, 3.21, 3.31, 3.31, 3.34 to 3.37, 3.41, 3.43, 3.48 to 3.52, 3.54, 3.77 to 3.98 and 3.101 to 3.103, in particular, exhibit an activity of over 80%.

Example B3

Activity Against *Diabrotica balteata* Larvae

Maize seedlings are sprayed with an aqueous emulsion spray mixture which comprises 400 ppm of the active ingredient. After the spray coating has dried on, the maize seedlings are populated with 10 second instar larvae of *Diabrotica balteata* and introduced into a plastic container. 6 days later, the test is evaluated. The percentage reduction in population (% activity) is determined by comparing the number of dead larvae on the treated plants with those on the untreated plants.

In this test, compounds of Tables 3 to 29 are very effective. Compounds nos. 3.2 to 3.4, 3.7, 3.8, 3.10, 3.20, 3.21, 3.29 to 3.32, 3.34 to 3.37, 3.41, 3.43, 3.48, 3.49, 3.50 to 3.52, 3.77 to 3.80, 3.82 to 3.87, 3.90 to 3.98 and 3.100 to 3.103, in particular, exhibit an activity of over 80%.

Example B4

Activity Against *Plutella xylostella* Caterpillars

Young cabbage plants are sprayed with an aqueous emulsion spray mixture which comprises 400 ppm of the active ingredient. After the spray coating has dried on, the cabbage plants are populated with 10 third instar caterpillars of *Plutella xylostella* and introduced into a plastic container. 3 days later, the test is evaluated. The percentage reduction in population, or the percentage reduction in feeding damage (% activity), is determined by comparing the number of dead caterpillars and the feeding damage on the treated plants with those on the untreated plants.

In this test, compounds of Tables 3 to 29 are very effective. Compounds nos. 3.2 to 3.4, 3.7, 3.18, 3.20, 3.21, 3.26, 3.29 to 3.32, 3.34 to 3.37, 3.41, 3.43, 3.48, 3.49, 3.50 to 3.52, 3.54, 3.77 to 3.98, 3.101 and 3.103, in particular, exhibit an activity of over 80%.

Example B5

Activity Against *Tetranychus urticae*

Young bean plants are populated with a mixed population of *Tetranychus urticae* and, 1 day later, sprayed with an aqueous emulsion spray mixture which comprises 400 ppm of the active ingredient. The plants are subsequently incubated for 6 days at 25° C. and then evaluated. The percentage reduction in population (% activity) is determined by comparing the number of dead eggs, larvae and adults on the treated plants with those on the untreated plants.

In this test, compounds of Tables 3 to 29 are very effective. Compounds nos. 3.3, 3.17, 3.18, 3.20, 3.21, 3.29, 3.30, 3.34 to 3.37, 3.41, 3.48 to 3.52, 3.77, 3.78, 3.80, 3.82 to 3.92, 3.94, 3.95, 3.97, 3.98 and 3.101 to 3.103, in particular, exhibit an activity of over 80%.

Example B6

Activity Against *Heliothis virescens* Caterpillars

Young soya plants are sprayed with an aqueous emulsion spray mixture which comprises 400 ppm of the active ingredient. After the spray coating has dried on, the soya plants are populated with 10 first instar caterpillars of Heliothis virescens and introduced into a plastic container. 6 days later, the test is evaluated. The percentage reduction in population, or the percentage reduction in feeding damage (% activity), is determined by comparing the number of dead caterpillars and the feeding damage on the treated plants with those on the untreated plants.

In this test, compounds of Tables 3 to 29 are very effective. Compounds nos. 3.2 to 3.4, 3.18, 3.20, 3.21, 3.29, 3.30, 3.32, 3.34, 3.35, 3.36, 3.41, 3.48 to 3.51, 3.54, 3.77 to 3.80, 3.82 to 3.85, 3.90 to 3.92, 3.94 to 3.98 and 3.101 to 3.103, in particular, exhibit an activity of over 80%.

Example B7

Activity Against *Panonychus ulmi* (OP- and Carb.-Resistant)

Apple seedlings are populated with adult females of *Panonychus ulmi*. After 7 days, the infected plants are sprayed to drip point with an aqueous emulsion spray mixture comprising 400 ppm of the compound to be tested and grown in a greenhouse. After 14 days, the test is evaluated. The percentage reduction in population (% activity) is determined by comparing the number of dead spider mites on the treated plants with those on the untreated plants.

In this test, compounds of Tables 3 to 29 are very effective. Compounds nos. 3.34, 3.77, 3.78, 3.80 and 3.90 to 3.92, in particular, exhibit an activity of over 80%.

Example B8

Activity Against *Aphis craccivora*

Pea seedlings are infected with *Aphis craccivora* and subsequently sprayed with a spray mixture which comprises 400 ppm of the active ingredient and incubated at 20° C. 3 and 6 days later, respectively, the test is evaluated. The percentage reduction in population (% activity) is determined by comparing the number of dead aphids on the treated plants with those on the untreated plants.

In this test, compounds of Tables 3 to 29 are very effective. Compounds nos. 3.41, 3.77, 3.90 3.92, 3.95, 3.97, 3.98 and 3.106, in particular, exhibit an activity of over 80%.

Example B9

Activity Against *Myzus persicae*

Pea seedlings are infected with *Myzus persicae* and subsequently sprayed with a spray mixture which comprises 400 ppm of the active ingredient and incubated at 20° C. 3 and 6 days later, respectively, the test is evaluated. The percentage reduction in population (% activity) is determined by comparing the number of dead aphids on the treated plants with those on the untreated plants.

In this test, compounds of Tables 3 to 29 are very effective. Compounds nos. 3.77, 3.90, 3.92, 3.97 and 3.98, in particular, exhibit an activity of over 80%.

Example B10

Activity Against *Nilaparvata lugens*

Rice plants are treated with an aqueous emulsion spray mixture which comprises 400 ppm of the active ingredient. After the spray coating has dried on, the rice plants are populated with 2nd and 3rd instar larvae of *Nilaparvata lugens*. 21 days later, the test is evaluated. The percentage reduction in population (% activity) is determined by comparing the number of surviving leaf hoppers on the treated plants with those on the untreated plants.

In this test, compounds of Tables 3 to 29 are very effective. Compounds nos. 3.18, 3.20, 3.30, 3.51, 3.77, 3.80, 3.92 and 3.98, in particular, exhibit an activity of over 80%.

Example B11

Activity Against *Frankliniella occidentalis*

Bell pepper plants in the greenhouse which are populated with a natural mixed population of larvae, nymphs and adults of *Frankliniella occidentalis* are sprayed three times to drip point at 10-day intervals with a spray mixture which comprises 10 g/hl of the compound of the formula I. Immediately prior to the second and one day after the third treatment, the nymphs on the treated plants and on untreated control plants are counted, and the reduction in the number of nymphs is determined.

In this test, compounds of Tables 3 to 29 are very effective. Compounds nos. 3.2, 3.18, 3.20 3.48, 3.77, 3.79, 3.80, 3.84, 3.89, 3.90 and 3.91, in particular, exhibit an activity of over 80%.

What is claimed is:

1. The compound having the formula

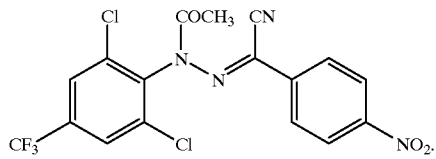

2. An insecticidal and acaricidal composition which comprises an insecticidally or acaricidally effective amount of at least one compound of the formula

(I)

in which
  $A_1$ and $A_2$ are independent of one another and are in each case a mono- or bicyclic aryl;
  $A_1$ is substituted with a substituent $(R_{3a})_{n1}$ and $A_2$ with a substituent $(R_{3b})_{n2}$;
  $R_1$ is —CN;
  $R_2$ is hydrogen, —OH, $C_1$–$C_6$alkyl, $C_1$–$C_6$alkoxy, $C_3$–$C_6$cycloalkyl, $C_3$–$C_6$alkenyl, $C_3$–$C_6$alkynyl, halo- $C_1$–$C_6$alkyl, halo-$C_3$–$C_6$alkenyl, halo-$C_3$–$C_6$alkynyl, benzyl or benzoyl, in which the benzyl or benzoyl radical is unsubstituted or mono- to trisubstituted in the aromatic ring by substituents which are independent of one another and selected from the group consisting of halogen, —CN, $NO_2$, $C_1$–$C_6$alkyl, $C_1$–$C_6$alkoxy, halo-$C_1$–$C_6$alkyl and halo-$C_1$–$C_6$alkoxy; $C_1$–$C_6$alkoxy-$C_1$–$C_6$alkyl, cyano-$C_1$–$C_6$alkyl, —C(=X)—$R_7$, —OC(=O)—$R_7$, —C(=O)—C(=O)—$R_7$, —S(=O)$_p$N($R_6$)$_2$ wherein the two $R_6$ groups may be the same or different; cyano, —$C_1$–$C_6$alkyl-N($R_{10}$)—C(=O)—$R_8$, —$C_1$–$C_6$alkyl-S—C(=S)—$R_8$, —$C_1$–$C_6$alkyl-S(=O)$_p$—$R_9$, —S(=O)$_p$—$R_9$, or —$CH_2$—N($R_{10}$)—$SO_2$—$R_9$;

$R_{3a}$ and $R_{3b}$ are independently of each other halogen, $C_1$–$C_6$alkyl, $C_2$–$C_4$alkenyl, $C_2$–$C_4$alkynyl, halo-$C_1$–$C_6$alkyl, halo-$C_2$–$C_4$alkenyl, halo-$C_2$–$C_4$alkynyl, $C_1$–$C_6$alkoxy, halo-$C_1$–$C_6$alkoxy, $C_2$–$C_6$alkenyloxy, $C_2$–$C_6$alkynyloxy, halo-$C_2$–$C_6$alkenyloxy, halo-$C_2$–$C_6$alkynyloxy, —$SF_5$, —CHO, —C(=O)—$C_1$–$C_6$alkyl, —C(=O)-halo-$C_1$–$C_6$alkyl, —C(=O)—$OC_1$–$C_6$alkyl, —C(=O)—O-halo-$C_1$–$C_6$alkyl, —O—C(=O)N($R_6$)$_2$ wherein the two $R_6$ groups may be the same or different, —CN, —$NO_2$, —S(=O)$_2$N($R_6$)$_2$ wherein the two $R_6$ groups may be the same or different, —S(=O)$_p$—$C_1$–$C_6$alkyl, —S(=O)$_p$-halo-$C_1$–$C_6$alkyl, —O—S(=O)$_p$—$C_1$–$C_6$alkyl, —O—S(=O)$_p$-halo-$C_1$–$C_6$alkyl, phenyl, benzyl, phenoxy or benzyloxy, each of the phenyl, benzyl, phenoxy or benzyloxy radicals being unsubstituted or mono- to pentasubstituted in the aromatic ring by substituents which are independent of one another and selected from the group consisting of halogen, cyano, $NO_2$, $C_1$–$C_6$alkyl, halo-$C_1$–$C_6$alkyl, $C_1$–$C_6$alkoxy and halo-$C_1$–$C_6$alkoxy;

$n_1$ is 3 or 4;

$n_2$ is 1 or 2;

X is O or S;

p is 0, 1 or 2;

$R_5$ radicals independently of one another are H or $C_1$–$C_8$alkyl;

$R_6$ radicals independently of one another are H, $C_1$–$C_8$alkyl, $C_3$–$C_6$cycloalkyl, phenyl or benzyl, the phenyl or benzyl group in the aromatic ring being unsubstituted or mono- to trisubstituted by substituents which are independent of one another and selected from the group consisting of halogen, —CN, $NO_2$, $C_1$–$C_6$alkyl, $C_1$–$C_4$alkoxy, halo-$C_1$–$C_6$alkyl and halo-$C_1$–$C_6$alkoxy; or two alkyl radicals $R_6$ together with the nitrogen atom to which they are bonded form a five- to seven-membered ring in which a $CH_2$ group may be replaced by a hetero atom selected from the group consisting of O and S, or by NH, and where the five- to seven-membered ring is unsubstituted or mono- or disubstituted by $C_1$–$C_4$alkyl;

$R_7$ is H, $C_1$–$C_8$alkyl, $C_2$–$C_8$alkenyl, halo-$C_1$–$C_8$alkyl, halo-$C_2$–$C_8$alkenyl, $C_1$–$C_8$alkoxy, halo-$C_1$–$C_8$alkoxy, $C_3$–$C_6$cycloalkyl, phenyl, benzyl, phenoxy, benzyloxy or —N($R_6$)$_2$ wherein the two $R_6$ groups may Pe the same or different;

$R_8$ is $C_1$–$C_8$alkyl, $C_1$–$C_8$alkoxy, halo-$C_1$–$C_8$alkyl, halo-$C_1$–$C_8$alkoxy, $C_1$–$C_8$alkylthio, phenyl, benzyl or —N($R_6$)$_2$ wherein the two $R_6$ groups may be the same or different;

$R_9$ is $C_1$–$C_6$alkyl, halo-$C_1$–$C_4$alkyl or aryl which is unsubstituted or mono- to trisubstituted by substituents which are independent of one another and selected from the group consisting of $C_1$–$C_6$alkyl, $C_2$–$C_4$alkenyl, $C_2$–$C_4$alkynyl, $C_1$–$C_4$alkoxy, halogen, cyano, halo-$C_1$–$C_4$alkyl, halo-$C_2$–$C_4$alkenyl, halo-$C_2$–$C_4$alkynyl, halo-$C_1$–$C_4$alkoxy and nitro; and $R_{10}$ is H, $C_1$–$C_4$alkyl, $C_3$–$C_6$cycloalkyl, phenyl or benzyl, the phenyl and benzyl radicals being unsubstituted or mono- to trisubstituted in the aromatic ring by substituents which are independent of one another and selected from the group consisting of $C_1$–$C_4$alkyl, $C_1$–$C_4$alkoxy, halogen, cyano, halo-$C_1$–$C_4$alkyl, halo-$C_1$–$C_4$alkoxy and nitro;

or, an E/Z isomer, E/Z isomer mixtures and/or tautomers thereof, in each case in free form or in salt form.

3. A method of controlling insects and representatives of the order Acarina, which comprises applying an insecticidally or acaricidally effective amount of a composition as described in claim 2 to the insects, to the representatives of the order Acarina, or to their environment.

4. A method for the protection of plant propagation material against attack by insects and representatives of the order Acarina, which comprises treating the propagation material or the site where the propagation material is planted with an insecticidally or acaricidally effective amount of a composition as described in claim 2.

* * * * *